US005550276A

United States Patent [19]
Wirth et al.

[11] Patent Number: 5,550,276
[45] Date of Patent: Aug. 27, 1996

[54] PHOSPHONIC ACID DERIVATIVES AND THIONOPHOSPHONIC ACID DERIVATIVES

[75] Inventors: Hermann O. Wirth, Bensheim; Hans-Helmut Friedrich, Lautertal; Kay S. Gröninger, Darmstadt, all of Germany

[73] Assignee: Ciba-Geigy Corporation, Tarrytown, N.Y.

[21] Appl. No.: 483,624

[22] Filed: Jun. 7, 1995

Related U.S. Application Data

[63] Continuation of Ser. No. 90,980, Jul. 12, 1993, abandoned, which is a continuation of Ser. No. 954,943, Sep. 30, 1992, abandoned, which is a continuation of Ser. No. 793,495, Nov. 14, 1991, abandoned, which is a continuation of Ser. No. 641,197, Jan. 15, 1991, abandoned.

[30] Foreign Application Priority Data

Jan. 18, 1990 [CH] Switzerland ............... 162/90

[51] Int. Cl.$^6$ ............ C07F 9/141; C07F 9/201
[52] U.S. Cl. .......... 558/177; 544/195; 544/214; 544/219; 558/73; 558/81; 558/151; 558/195; 558/196; 558/197; 558/198; 558/199; 558/200; 558/207; 558/205
[58] Field of Search .............. 544/195, 214, 544/219; 558/73, 81, 151, 156, 195, 196, 197, 198, 199, 200, 207

[56] References Cited

U.S. PATENT DOCUMENTS

| | | | |
|---|---|---|---|
| 4,186,157 | 1/1980 | Ripple | 558/108 |
| 4,413,125 | 11/1983 | Gaertner | 546/22 |
| 4,472,577 | 9/1984 | Lantzsch | 558/197 |
| 4,475,943 | 10/1984 | Gaertner | 71/86 |
| 4,746,654 | 5/1988 | Breliere et al. | 558/155 |
| 4,876,248 | 10/1989 | Breliere et al. | 514/108 |
| 4,959,167 | 9/1990 | Dubas | 252/32.7 |

FOREIGN PATENT DOCUMENTS

| | | |
|---|---|---|
| 0328488 | 8/1989 | European Pat. Off. . |
| 0804141 | 11/1958 | United Kingdom ............ 558/184 |
| 967627 | 8/1964 | United Kingdom . |
| 1068628 | 5/1967 | United Kingdom ............ 558/184 |

OTHER PUBLICATIONS

Ivin et al, "Chemical Abstract" 67(91, 1967 #43873n.
Hammer Schmidt et al "Chemical Abstract" 94(9), 1980 #64752V.
Hammer Schmidt et al. Chemical Abstract, 94(9), 1980 #64752V.
Ivin et al. Chemical Abstract, vol. 67 #43873, 1967.
F. Hammerschmidt et al. Monat. Chemie, 111, 1015 (1980).
Chem. Abst. 67, 43873n (1967).
B. Springs et al., J. Org. Chem. 41, 1165 (1976).
D. Redmore, Chem. Reviews 71, 315 (1971).

*Primary Examiner*—Yogendra N. Gupta
*Attorney, Agent, or Firm*—Luther A. R. Hall; William A. Teoli, Jr.; David R. Crichton

[57] ABSTRACT

Compounds of the general formula I $$\left[\begin{array}{c} R^1-O \\ \\ R^2-Q \end{array} \diagdown P \diagup \begin{array}{c} X \\ \\ Y-T \end{array}\right]_n R^4, \quad (I)$$

in which n is 1, 2 or 3 and in which X is oxygen or sulfur, T has the meaning of $-S-$, $-S-S-$, $-S-S-S-$, $-S-S-S-S-$, $-S-S-S-S-S-$, $$-\underset{\underset{O}{\overset{\overset{O}{\|}}{S}}}{\|}-, \quad -\underset{\underset{O}{\|}}{\overset{\overset{O}{\|}}{S}}- \quad \text{or} \quad -\underset{\underset{O}{\|}}{S}-\overset{\overset{O}{\|}}{S}-$$

and Y has the meaning of $$-\underset{\underset{R^3}{|}}{\overset{\overset{O-Z}{|}}{C}}-CH_2-$$

in which Z has the meaning of $-H$, $-COR^{13}$, $-COOR^{13}$ or $-CONHR^{13}$, and Q has the meaning of oxygen or $-NR^0-$, and $R^1$, $R^2$, $R^0$, $R^4$ and $R^{13}$ are as defined in claim 1, with the proviso that the compound of the formula $C_2H_5-S-CH_2CH(OH)-P(OC_2H_5)_2$ is excepted.

The invention also relates to compositions containing the compounds of the formula I and organic materials, for example functional liquids and, in particular, lubricants.

10 Claims, No Drawings

PHOSPHONIC ACID DERIVATIVES AND THIONOPHOSPHONIC ACID DERIVATIVES

This application is a continuation of Ser. No. 08/090,980, filed Jul. 12, 1993 now abandoned which is a continuation of Ser. No. 07/954,943, filed Sep. 30, 1992, now abandoned which is a continuation of Ser. No. 07/793,495, filed Nov. 14, 1991, now abandoned, which is a continuation of Ser. No. 07/641,197, filed Jan. 15, 1991, now abandoned.

The invention relates to novel compounds from the series of the phosphonic acids and thionophosphonic acid derivatives, to novel compositions containing these phosphonic acids and thionophosphonic acid derivatives, to novel preparation processes, and to the use of the sulfur-containing phosphonic acids and thionophosphonic acid derivatives in organic materials which are subjected to chemical, oxidative or actinic degradation.

For example, the compound of the formula $EtSCH_2CH(OH)PO(OEt)_2$, prepared from a molar mixture of $EtSCH_2CHO$ and $(EtO)_2PHO$ by treatment with EtONa/EtOH, has been disclosed in S. Z. Ivin and V. K. Promonenkov, Za. Obshch. Khim. 37(2), 489–92 (1967). The compound is said to have an insecticidal action on flies.

A process for the preparation of phosphorus-containing reaction products which can be employed as lubricant additives has been disclosed in U.S. Pat. No. 4,186,157.

Novel compounds, a novel process for their preparation, novel compositions and novel uses have now been found.

The compounds according to the invention have the general formula I

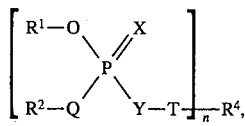  (I)

in which n is 1, 2 or 3 and in which X is oxygen or sulfur, T has the meaning of —S—, —S—S—, —S—S—S—, —S—S—S—S—, —S—S—S—S—S—,

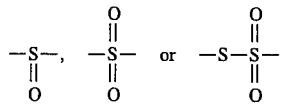

and Y has the meaning of

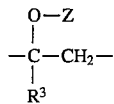

in which Z has the meaning of —H, —COR$^{13}$, —COOR$^{13}$ or —CONHR$^{13}$, and Q has the meaning of oxygen or —NR$^O$—, and R$^1$, R$^2$, R$^O$ and R$^{13}$ are identical or different and are an alkyl group having 1 to 18 C atoms, an alkenyl group having 2 to 18 C atoms, a phenyl or naphthyl group, a phenyl or naphthyl group each of which is substituted by at least one C$_1$–C$_4$alkyl group, or are a phenylalkyl group having 7 to 9 C atoms, a cycloalkyl group having 5 to 12 ring C atoms or a cycloalkyl group having 5 to 12 ring C atoms which is substituted by at least one alkyl group having 1 to 4 C atoms, or R$^O$ is —H, or R$^1$ and R$^2$ together are a straight-chain alkylene group having 2 to 5 C atoms, a straight-chain alkylene group having 2 to 5 C atoms which is substituted by at least one alkyl group having 1 to 8 C atoms or by at least one group —CH$_2$—O—C$_1$–C$_{12}$alkyl or —CH$_2$—S—C$_1$–C$_{12}$alkyl, or R$^1$ and R$^2$ together are a group of the formula

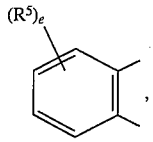

in which R$^5$ is an alkyl group having 1 to 4 C atoms and e is a number 0, 1 or 2, or R$^1$ and R$^2$ together are a group of the formula

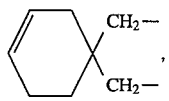

R$^3$ has the meaning of —H, alkyl having 1 to 4 C atoms, phenyl, —CH$_2$—S—R$^{4'}$ in which R$^{4'}$ is as defined below, or is phenyl or phenyl substituted by at least one alkyl group having 1 to 4 C atoms, and, if n is 1, R$^4$ has the meaning of R$^{4'}$ in which R$^{4'}$ is —H, an alkyl group having 1 to 18 C atoms, an alkenyl group having 2–18 C atoms, a phenyl or naphthyl group, a phenyl or naphthyl group which is substituted by at least one C$_1$–C$_9$alkyl group, or is a phenylalkyl group having 7 to 9 C atoms, pinan-10-yl, an alkyl group having 1 to 18 C atoms which is substituted by at least one OH group, an alkyl group having 2 to 18 C atoms which is interrupted by at least one —S— or —O—, an alkyl group having 3 to 18 C atoms which is substituted by at least one OH group and interrupted by at least one —S— or —O—, a group of the formula —R$^6$—COOR$^7$ in which R$^6$ is an alkylene group having 1 to 6 C atoms and R$^7$ is an alkyl group having 1 to 12 C atoms; a cycloalkyl group having 5 to 12 ring C atoms, a cycloalkyl group having 5 to 12 ring C atoms which is substituted by at least one alkyl group having 1 to 4 C atoms, or is a cycloalkyl group having 5 to 12 ring C atoms which is interrupted by at least one —O— or —S—, or is a cycloalkyl group having 5 to 12 ring C atoms which is substituted by at least one alkyl group having 1 to 4 C atoms and interrupted by at least one —O— or —S—, or R$^{4'}$ is a group of the formula

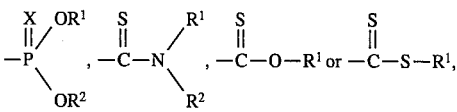

in which X is oxygen or sulfur and Q, R$^1$ and R$^2$ are as defined above, or R$^{4'}$ is a heterocycle having 5 to 6 ring members with 1 to 4 members from the series comprising —NH—,

—N= or —N(Q—C$_4$alkyl)-, or a heterocycle having 5 to 6 ring members with one or two members from the series comprising —NH—, —N=,

or —N(C$_1$–C$_4$alkyl)— and one further hetero atom from the series comprising O or S, or the abovementioned heterocycles which are fused to a benzene radical, or the above-mentioned heterocycles which are substituted on one or two of the C atoms by =S and/or $C_1$–$C_4$alkyl, or $R^{4'}$ has the meaning of

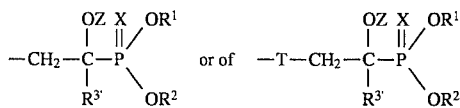

in which T and Z are as defined above, X is oxygen or sulfur, $R^{3'}$ is —H, alkyl having 1 to 4 C atoms, phenyl or phenyl which is substituted by at least one alkyl group having 1 to 9 C atoms, and Q, $R^1$ and $R^2$ are as defined above, or $R^4$ has the meaning of

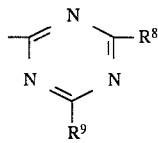

in which $R^8$ and $R^9$, independently of one another, are $C_1$–$C_{18}$alkyl, phenyl, phenyl which is mono-, di- or tri-$C_1$–$C_4$alkyl-substituted, or are a group —$OR^{10}$, —$SR^{10}$ or

in which $R^{10}$ is $C_1$–$C_{18}$alkyl, $C_5$–$C_{12}$cycloalkyl, $C_5$–$C_{12}$cycloalkyl which is mono-, di- or tri-$C_1$–$C_4$alkyl-substituted, or is $C_3$–$C_6$alkenyl, phenyl, phenyl which is mono-, di- or tri-$C_1$–$C_9$alkyl-substituted, or is $C_7$–$C_9$phenylalkyl or $C_7$–$C_9$phenylalkyl which is mono-, di- or tri-$C_1$–$C_4$alkyl-substituted on the phenyl, and $R^{11}$ and $R^{12}$ which are identical or different are —H, $C_1$–$C_{18}$alkyl, $C_5$–$C_{12}$cycloalkyl, $C_5$–$C_{12}$cycloalkyl which is mono-, di- or tri-$C_1$–$C_4$alkyl-substituted, or are $C_3$–$C_6$alkenyl, $C_7$–$C_9$phenylalkyl, $C_7$–$C_9$phenylalkyl which is mono-, di- or tri-$C_1$–$C_4$alkyl-substituted on the phenyl, or are $C_2$–$C_4$alkyl which is substituted by —OH, by $C_1$–$C_4$alkoxy or by di($C_1$–$C_4$alkyl)amino, or $R^{11}$ and $R^{12}$ together with the nitrogen atom linking them are a 5- to 7-membered heterocycle, or, if n is 2, $R^4$ is straight-chain alkylene having 1 to 12 C atoms or alkenylene having 2 to 10 C atoms or straight-chain alkylene having 1 to 10 C atoms which is substituted by at least one alkyl group having 1 to 4 C atoms, or straight-chain alkylene having 2 to 10 C atoms which is interrupted by at least one —S— or —O—, or straight-chain alkylene having 2 to 10 C atoms which is substituted by at least one alkyl group having 1 to 4 C atoms and interrupted by at least one —S— or —O—, or $R^4$ has the meaning of a bivalent heterocycle having 5 to 6 ring members with 1 to 4 nitrogen atoms, or of a bivalent heterocycle having 5 to 6 ring members with one or two nitrogen atoms and one further hetero atom from the series comprising O or S, or of the abovementioned bivalent heterocycles which are fused to a benzo radical, or of the abovementioned bivalent heterocycles which are substituted by =S and/or $C_1$–$C_4$alkyl on one or two of the C atoms, or, $R^4$ has the meaning of

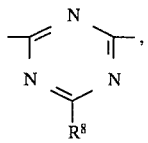

in which $R^8$ is as defined above, or, if n is 3, $R^4$ is a group of the formula

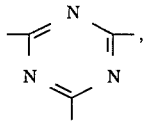

with the proviso that the compound of the formula $C_2H_5$—S—$CH_2CH(OH)$—$PO(—O—C_2H_5)_2$ is excepted.

In the compounds of the formula I T expediently has the meaning of —S—, —S—S—,

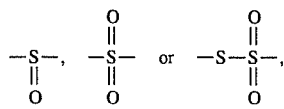

preferably —S—, —S—S,

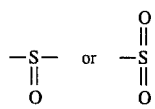

and particularly preferably —S or

Expedient compounds of the formula I are those in which n is 1, 2 or 3, and in which $R^1$ and $R^2$ are identical or different and are an alkyl group having 1 to 18 C atoms, an alkenyl group having 2 to 18 C atoms, a phenyl group, a phenyl group which is substituted by one or two $C_1$–$C_9$alkyl groups, or are a phenylalkyl group having 7 to 9 C atoms, a cycloalkyl group having 5 to 12 ring C atoms or a cycloalkyl group having 5 to 12 ring C atoms which is substituted by an alkyl group having 1 to 4 C atoms, or in which $R^1$ and $R^2$ together are a straight-chain alkylene group having 2 to 5 C atoms, a straight-chain alkylene group having 2 to 5 C atoms which is substituted by one or two alkyl groups having 1 to 4 C atoms or by a group —$CH_2$—O—$C_1$–$C_9$alkyl or —$CH_2$—S—$C_1$–$C_9$alkyl, or $R^1$ and $R^2$ together are a group of the formula

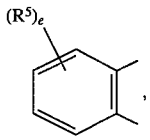

in which $R^5$ is an alkyl group having 1 to 4 C atoms and e is a number 0, 1 or 2, or $R^1$ and $R^2$ together are a group of the formula

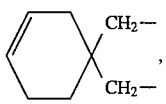

$R^3$ has the meaning of -H, alkyl having 1 to 4 C atoms, —CH$_2$—S—R$^{4'}$ in which R$^{4'}$ is as defined below, phenyl or phenyl which is substituted by an alkyl group having 1 to 9 C atoms, and, if n is 1, $R^4$ has the meaning of R$^{4'}$ in which R$^{4'}$ is —H, an alkyl group having 1 to 18 C atoms, an alkenyl group having 2 to 18 C atoms, a phenyl group, a phenyl group which is substituted by at least one C$_1$–C$_9$alkyl group, or is a phenylalkyl group having 7 to 9 C atoms, an alkyl group having 1 to 18 C atoms which is substituted by 1 to 5 OH groups, an alkyl group having 2 to 18 C atoms which is interrupted by 1 to 5 —S— or —O—, an alkyl group having 3 to 18 C atoms which is substituted by 1 to 5 OH groups and interrupted by 1 to 5 —S— or —O—, a cycloalkyl group having 5 to 12 ring C atoms, a cycloalkyl group having 5 to 12 ring C atoms which is substituted by an alkyl group having 1 to 4 C atoms, or R$^{4'}$ is a group of the formula

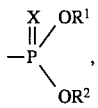

in which

X is oxygen or sulfur and R$^1$ and R$^2$ are as defined above, or

R$^{4'}$ has the meaning of a heterocycle having 5 to 6 ring members with 1 to 3 members from the series comprising —NH—,

or —N(CH$_3$)— or of a heterocycle having 5 to 6 ring members with one member from the series comprising —NH—, —N=,

or —N(CH$_3$)— and one further hetero atom from the series comprising O or S, or of the abovementioned heterocycles which are fused to a benzo radical, or of the abovementioned heterocycles which are substituted on one or two of the C atoms by =S and/or C$_1$–C$_4$alkyl, or, if n is 2, $R^4$ is straight-chain alkylene having 1 to 10 C atoms or straight-chain alkylene having 1 to 10 C atoms which is substituted by one or two alkyl groups having 1 to 4 C atoms, or straight-chain alkylene having 2 to 10 C atoms which is interrupted by 1 to 5 —S— or —O—, or alkylene having 2 to 10 C atoms which is substituted by one or two alkyl groups having 1 to 4 C atoms and interrupted by 1 to 5 —S— or —O—, or R$^4$ has the meaning of a bivalent heterocycle having 5 to 6 ring members with 1 to 3 nitrogen atoms, or of a bivalent heterocycle having 5 to 6 ring members with one or two nitrogen atoms and one further hereto atom from the series comprising O or S, or of the abovementioned bivalent heterocycles which are fused to a benzo radical, or of the abovementioned bivalent heterocycles which are substituted on one or two of the C atoms by =S and/or C$_1$–C$_4$alkyl, or, if n is 3, $R^4$ is a group of the formula

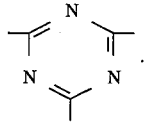

Other expedient compounds of the formula I are those in which R$^1$ and R$^2$ are identical or different and are an alkyl group having 2 to 12 C atoms, phenyl, phenyl which is substituted by one C$_1$–C$_9$alkyl group, benzyl, or a cycloalkyl group having 5 to 10 ring C atoms, or in which R$^1$ and R$^2$ together are a straight-chain alkylene group having 2 to 4 C atoms or a straight-chain alkylene group having 2 to 4 C atoms which is substituted by one or two alkyl groups each of which has 1 to 4 C atoms, or which is substituted by a group of the formula —CH$_2$—S—C$_4$H$_9$, or are a group of the formula

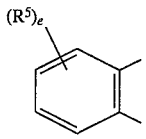

in which e is 0 or 1 and, if e is 1, R$^5$ is tert-butyl.

Preferred compounds of the formula I are those in which R$^1$ and R$^2$ are identical or different and are a straight-chain or branched-chain alkyl group having 2 to 12 C atoms, phenyl or cyclohexyl, or R$^1$ and R$^2$ together are a straight-chain C$_2$- or C$_3$-alkylene group, or are a dimethylene or trimethylene group which is substituted by a C$_1$–C$_4$alkyl group, or are a di-C$_1$–C$_4$alkyl-substituted dimethylene or trimethylene group or a —CH$_2$—S—t—C$_4$H$_9$-substituted dimethylene or trimethylene group, or a group of the formula

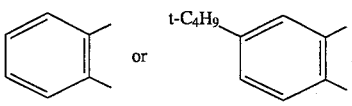

Particularly preferred compounds of the formula I am those in which R$^1$ and R$^2$ are identical or different and are C$_2$–C$_8$alkyl and, in particular, ethyl, i-propyl, n-butyl, t-butyl, 2-ethylhexyl or n-octyl, or R$^1$ and R$^2$ together are dimethylene, 1-methyldimethylene, 1-ethyldimethylene, 2,2-dimethyltrimethylene or 2-ethyl-2-n-butyltrimethylene.

Furthermore, the particularly preferred compounds of the formula I include those in which R$^1$ and R$^2$ are identical.

Expedient compounds of the formula I are those in which R$^3$ is methyl, phenyl or —CH$_3$–S—R$^{4''}$ in which R$^{4''}$ is an alkyl group having 2 to 12 C atoms or

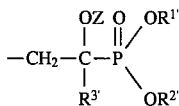

in which Z is as defined above and R$^{3'}$ is —H, alkyl having 1 to 4 C atoms or phenyl, and R$^{1'}$ and R$^{2'}$ are identical and an alkyl group having 1 to 8 C atoms, phenyl or cyclohexyl, or R$^{1'}$ and R$^{2'}$ together are a straight-chain C$_2$- or C$_3$-alkylene group or a C$_1$–C$_4$alkyl-substituted dimethylene or trimethylene group, a di-$C_1$-$C_4$alkyl-substituted dimethylene or trimethylene group or a —$CH_2$—S—t—$C_4H_9$- or —$CH_2$—O—$iC_8H_{17}$-substituted dimethylene or trimethylene group.

Expedient compounds of the formula I are those in which $R^{4'}$ is an alkyl group having 1 to 12 C atoms, a phenyl group, a benzyl group or an alkyl group having 2 to 8 C atoms which is substituted by an OH group or an alkyl group having 2 to 12 C atoms which is interrupted by an —O— or —S—, or an alkyl group having 2 to 18 C atoms which is interrupted by an —O— or —S— and substituted by an —OH group, or a group of the formula —$R_6$—$COOR^7$ in which $R^6$ is a straight-chain alkylene group having 1 to 3 C atoms and $R^7$ is an alkyl group having 4 to 8 C atoms, or is a cyclohexyl group, or $R^{4'}$ is a group of the formula

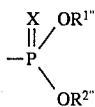

in which X is oxygen or sulfur and $R^{1'''}$ and $R^{2'''}$ are identical and are alkyl having 1 to 8 C atoms or $R^{1'''}$ and $R^{2'''}$ together are straight-chain alkylene having 2 or 3 C atoms or straight-chain alkylene having 2 or 3 C atoms which is substituted by one or two alkyl groups having 1 to 4 C atoms, or $R^{4'}$ has the meaning of a heterocycle having 5 to 6 ring members with 1 to 3 nitrogen atoms, or of a heterocycle having 5 to 6 ring members with one nitrogen atom and one further hetero atom from the series comprising O or S, or of the abovementioned heterocycles which are fused to a benzo radical, or of the abovementioned heterocycles which are substituted on one or two of the C atoms by =S or by $C_1$-$C_4$alkyl, or $R^{4'}$ has the meaning of

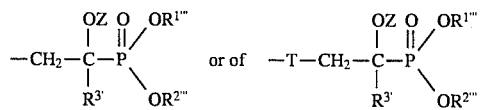

in which T and Z are as defined above, $R^{3'}$ is methyl and $R^{1'''}$ and $R^{2'''}$ are identical and are alkyl having 1 to 8 C atoms.

If $R^{4'}$ has the meaning of a heterocycle having 5 to 6 ring members with 1 to 3 nitrogen atoms or of a heterocycle having 5 to 6 ring members with one or two nitrogen atoms and one further hetero atom, the nitrogen atoms can be, for example, —NH— or —N—.

Preferred compounds of the formula I are those in which n is 2 and in which $R^4$ is straight-chain alkylene having 2 to 4 C atoms or $R^4$ has the meaning of a divalent heterocycle having 5 to 6 ring members with one or two nitrogen atoms and one further atom from the series comprising O or S.

Very particularly preferred compounds of the formula I are those in which n is 1, $R^1$ and $R^2$ are identical and are $C_1$-$C_{12}$alkyl, or $R^1$ and $R^2$ together are

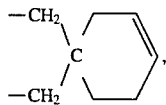

$R^3$ has the meaning of $C_1$-$C_4$alkyl or phenyl, and $R^4$ has the meaning of $R^{4'}$ in which $R^{4'}$ is $C_1$-$C_4$alkyl, a heterocycle having 5 ring members and one or two nitrogen atoms, a heterocycle having 5 ring members and one nitrogen atom and with one or two additional hereto atoms front the series comprising S or O, one of the abovementioned heterocycles with fused benzo ring, or $C_3$-$C_{12}$alkyl which is substituted by one —OH and interrupted by 1 or 2 O or S.

If $R^0$, $R^1$, $R^2$, $R^8$, $R^9$, $R^{10}$, $R^{11}$, $R^{12}$ and $R^{13}$ in compounds of the formula I are alkyl having 1 to 18 C atoms, then examples which may be mentioned are methyl, ethyl, propyl, isopropyl, n-butyl, isobutyl, t-butyl, pentyl, isopentyl, hexyl, heptyl, 3-heptyl, 1-octyl, 2-octyl, 2-ethylhexyl, nonyl, decyl, undecyl, dodccyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 3,5,5-trimethylhexyl, 1,1,3,3-tetramethylhexyl and 1-methylundecyl. Expedient alkyl radicals are those having 1 to 12 C atoms, which correspondingly can be seen from the examples above. Preferred alkyl groups are those having 1 to 12 C atoms, examples of which can again be seen correspondingly from the above enumeration. Particularly preferred are ethyl, i-propyl, n-butyl, t-butyl, 2-ethylhexyl, n-octyl and dodecyl for $R^1$ and $R^2$.

Examples of a phenyl or naphthyl group which are substituted by at least one $C_1$-$C_9$, as radicals $R^0$, $R^1$ or $R^2$, or of $R^8$, $R^9$, $R^{10}$, $R^{11}$, $R^{12}$ and $R^{13}$ as mono-, di- or tri-$C_1$-$C_9$alkyl-substituted phenyl are methylphenyl, dimethylphenyl, trimethylphenyl, ethylphenyl, isopropylphenyl, t-butylphenyl, di-t-butylphenyl, 2,6-di-t-butyl-4-methylphenyl or nonylphenyl.

Examples of a phenylalkyl group having 7 to 9 C atoms in the case of $R^0$, $R^1$, $R^2$, $R^{10}$, $R^{11}$, $R^{12}$ and $R^{13}$ are benzyl and 2-phenylethyl, benzyl being preferred. Examples of $R^{10}$, $R^{11}$, and $R^{12}$ as $C_7$-$C_9$phenylalkyl which is mono-, di- or tri-$C_1$-$C_4$alkyl-substituted on the phenyl are methylbenzyl, dimethylbenzyl and t-butylbenzyl.

If $R^0$, $R^1$, $R^2$, $R^{10}$, $R^{11}$, $R^{12}$ and $R^{13}$ is a cycloalkyl group having 5 to 12 ring C atoms, then examples which may be mentioned are cyclopentyl, cyclohexyl, cyclooctyl, cyclononyl, cyclodecyl, cycloundecyl and cyclododecyl, cyclohexyl being preferred.

If $R^0$, $R^1$, $R^2$ and $R^{13}$ are a cycloalkyl group having 5 to 12 ring C atoms which is substituted by at least one, expediently 1 to 3, preferably 1 or 2, alkyl groups having 1 to 4 C atoms, or if $R^{10}$, $R^{11}$ or $R^{12}$ are mono-, di- or tri-$C_1$-$C_4$alkyl-substituted $C_5$-$C_{12}$cycloalkyl groups, then examples which can be mentioned are methylcyclopentyl, dimethylcyclopentyl, 2- or 4-methylcyclohexyl, dimethylcyclohexyl, trimethylcyclohexyl or t-butylcyclohexyl. Cyclohexyl which is substituted by one alkyl group is preferred, for example methylcyclohexyl.

In addition to the abovementioned meanings of $R^0$, $R^0$ can also be —H.

If $R^1$ and $R^2$ together form a straight-chain alkylene group having 2 to 5 C atoms, then corresponding examples are ethylene, trimethylene, tetramethylene or pentamethylene. Ethylene and trimethylene are preferred.

If $R^1$ and $R^2$ together form a straight-chain alkylene group having 2 to 5 C atoms which is substituted by at least one alkyl group having 1 to 8 C atoms, then examples which may be mentioned are 1-methyl-1,2-ethanediyl, 1-ethyl- 1,2-ethanediyl, 2,2-dimethyl-1,3-propanediyl or 2-ethyl- 2-n-butyl- 1,3-propanediyl.

Alternatively, $R^1$ and $R^2$ together form, for example, a straight-chain alkylene group having 2 to 5 C atoms which is substituted by a group —$CH_2$—S—$C_1$-$C_9$alkyl. This is preferably a group of the formula

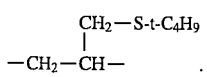

$R^1$ and $R^2$ together form a group of the formula

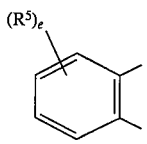

in which $R^5$ is an alkyl group having 1 to 4 C atoms and e is a number 0, 1 or 2, then preferred examples which may be mentioned are o-phenylene, 4-methyl-o-phenylene or 4-t-butyl-o-phenylene.

Q is —O— or —NR⁰—, —O— being preferred. Preferred for $R^0$ is —H or $C_1$–$C_4$alkyl, preferably t-butyl.

If Q is a radical —NR⁰—, then $R^1$ and $R^2$ together preferably form a dimethylene radical.

Correspondingly, the meanings of $R^{1'}$, $R^{1''}$, $R^{1'''}$, $R^{2'}$, $R^{2''}$ and $R^{2'''}$ can be seen in each case from the abovementioned lists. In the same molecule, the meanings of $R^1$ are expediently the same as for $R^{1'}$, $R^{1''}$ or $R^{1'''}$, respectively, and in the case of $R^2$, the same as in the case of $R^{2'}$, $R^{2''}$ or $R^{2'''}$.

If $R^{4'}$, $R^1$, $R^2$, $R^0$ or $R^{13}$ are an alkenyl group having 2 to 18 C atoms, then examples which may be mentioned are vinyl, allyl, 2-methallyl, 2-butenyl, trans-2-butenyl, 2-hexenyl, trans-2,4-hexadienyl, respectively hexenyl, decenyl, undecenyl, heptadecenyl, oleyl, cis-9-octadecenyl, trans-9-octadecenyl, cis,cis-9,12-octadecadienyl or cis,cis,cis-9,12, 15-octadecatrienyl.

Examples of $C_3$–$C_6$alkenyl in the case of $R^{10}$ are allyl and 2-methylallyl.

Examples of $R^{11}$ and $R^{12}$ as —OH-substituted $C_2$–$C_4$alkyl are 2-hydroxyethyl, 2-hydroxypropyl, 3-hydroxypropyl, 2-hydroxybutyl and 4-hydroxybutyl, with 2-hydroxyethyl being preferred.

Examples of $R^{11}$ and $R^{12}$ as $C_1$–$C_8$alkoxy-substituted $C_2$–$C_4$alkyl are 2-methoxyethyl, 2-ethoxyethyl, 3-methoxypropyl, 3-ethoxypropyl, 3-butoxypropyl, 3-octoxypropyl and 4-methoxybutyl. The methoxy group is preferred as the alkoxy group.

Examples of $R^{11}$ and $R^{12}$ as $C_2$–$C_4$alkyl, substituted by di($C_1$–$C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

If $R^{11}$ and $R^{12}$ together with the nitrogen atom linking them form a 5- to 7-membered heterocycle which, if desired, can also contain further hetero atoms from the series comprising N and O, then examples which may be mentioned are pyrrolidyl, piperidyl, piperazinyl, morpholinyl, N-methylpiperazinyl, hexahydroazepinyl and perhydroazepinyl.

The substituent $R^3$ in the formula I is, inter alia, alkyl having 1 to 4 C atoms. Examples are methyl, ethyl, n-propyl, i-propyl, n-butyl, 2-butyl or tert-butyl. Methyl is preferred.

If n is 1, the substituent $R^4$ in the formula I has, for example, the meaning of $R^{4'}$, which can be alkyl having 1 to 18 C atoms. Examples of such alkyl groups can be seen from the corresponding enumeration in the case of $R^1$ and $R^2$. n-Butyl, t-butyl, i-butyl, n-octyl, sec-octyl, t-nonyl, sec-dodecyl or t-dodecyl are preferred.

Examples and preferred versions of phenyl or naphthyl having at least one $C_1$–$C_4$alkyl group or of an aralkyl group having 7 to 9 C atoms as substituents $R^{4'}$ can be seen from the abovementioned enumerations in the case of $R^1$ and $R^2$.

Examples of $R^{4'}$, if this is an alkyl group having 1 to 18 C atoms which is substituted by at least one, expediently 1 to 5, OH group, or if this is an alkyl group having 2 to 18 C atoms which is interrupted by at least one, expediently 1 to 5, —S— or —O—, or if this is an alkyl group having 3 to 18 C atoms which is substituted by at least one, expediently 1 to 5, OH groups and interrupted by at least one, expediently 1 to 5, —S— or —O—, are 2-hydroxyethyl, 2-hydroxy-n-propyl, —CH$_2$—CH$_2$—CH$_2$— S—tC$_4$H$_9$, —CH$_2$—CH$_2$—CH$_2$—O—iC$_8$H$_{17}$, $$\begin{array}{c} CH_2-CH-CH_2-S\text{-}tC_4H_9 \\ | \\ OH \end{array} \text{ or}$$

$$\begin{array}{c} -CH_2-CH-CH_2-O\text{-}iC_8H_{17}. \\ | \\ OH \end{array}$$

If $R^{4'}$ is a group of the formula —R⁶COOR⁷, then $R^6$ is an alkylene group having 1 to 6 C atoms and $R^7$ is an alkyl group having 1 to 12 C atoms. Examples of $R^6$ are methylene, ethylene, trimethylene, tetramethylene or hexamethylene, examples of $R^7$ are methyl, ethyl, n-propyl, i-propyl, n-butyl, sec-butyl, tert-butyl, pentyl, hexyl, octyl, 2-ethylhexyl etc. Preferred examples of a group of the formula —R⁶COOR⁷ are —CH$_2$—COO—t—C$_4$H$_9$ or —CH$_2$COO—iC$_8$H$_{17}$.

If $R^{4'}$ is a cycloalkyl group having 5 to 12 ring C atoms or a cycloalkyl group having 5 to 12 ring C atoms which is substituted by at least one alkyl group having 1 to 4 C atoms, then corresponding examples and preferred versions can be found above, as mentioned by way of example in the case of $R^1$ and $R^2$.

If a substituent $R^{4'}$ has the formula

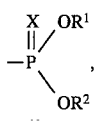

then X can be sulfur or oxygen, oxygen being preferred. $R^1$ and $R^2$ in such substituents can have the meanings and preferred versions mentioned at the outset. Preferred substituents of the above type are those in which $R^1$ and $R^2$ are identical. Preferred $R^1$ and $R^2$ in such substituents are $C_1$–$C_8$alkyl and, in particular, ethyl, n-butyl, i-butyl, n-octyl and 2-ethylhexyl. Further preferred meanings of $R^1$ and $R^2$ together are alkylene radicals and substituted alkylene radicals, ethylene and trimethylene as well as 2,2-dimethyl-1, 3-propanediyl being mentioned.

Accordingly, examples of the substituents with the above formula are:

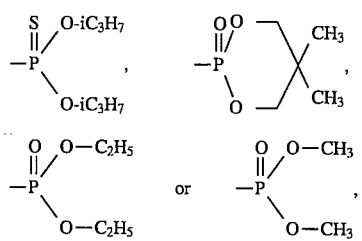

If $R^{4'}$ has the meaning of a heterocycle having 5 to 6 ring members with 1 to 4 members from the series comprising —NN—, —N=,

or —N($C_1$–$C_4$alkyl)— or of a heterocycle having 5 to 6 ring members with one or two members from the series comprising —NH—, —N═,

or —N($C_1$–$C_4$alkyl)— and: one further hetero atom from the series comprising O or S, or of the abovementioned heterocycles which are fused to a benzo radical, or of the abovementioned heterocycles which are substituted on one or two of the C atoms by ═S or $C_1$–$C_4$alkyl, then examples which may be mentioned are

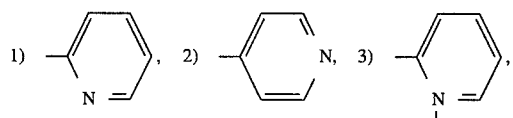

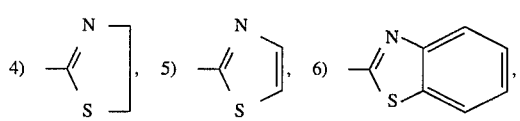

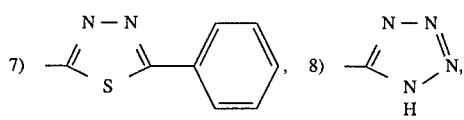

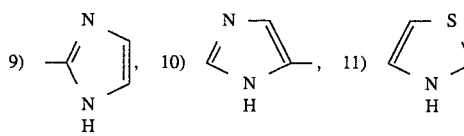

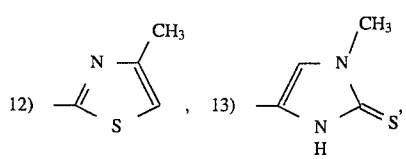

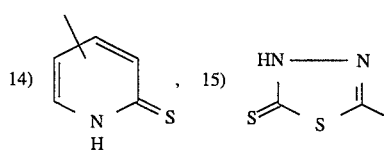

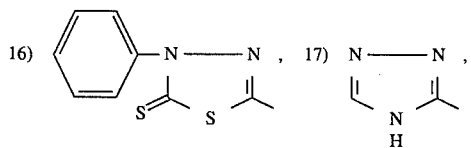

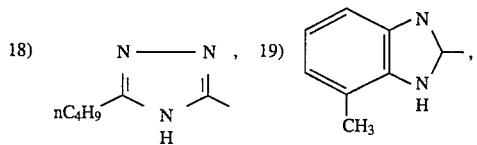

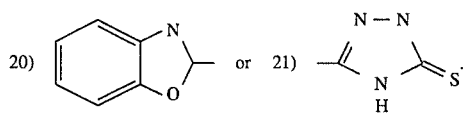

Preferred substituents from the above list are 1), 3), 4), 5), 6), 7), 8) and 9).

Expedient members of the series comprising —NH—, —N═,

or —N($C_1$–$C_4$alkyl)— are —NH—, —N═,

and —N($CH_3$)—, with —NH— and —N═ being preferred.

A further meaning of $R^4$ is a group of the formula

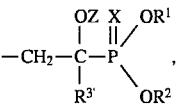

in which X is oxygen or sulfur, Z and $R^{3'}$ as well as $R^1$ and $R^2$ having the meanings mentioned at the outset. Preferred meanings in the case of $R^{3'}$ are —H, methyl and phenyl, and in the case of $R^1$ and $R^2$, which are preferably identical, alkyl groups having 1 to 8 C atoms or, for $R^1$ and $R^2$ together, a straight-chain alkylene group having 2 or 3 C atoms or straight-chain alkylene groups which have 2 or 3 C atoms and are substituted by one or two $C_1$–$C_4$alkyl groups. Z is preferably —H.

Examples of particularly preferred radicals are:

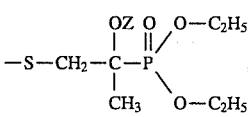

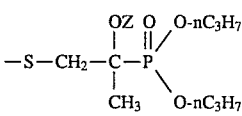

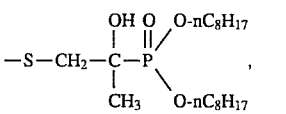

Z being as defined above and preferably being —H.

If, in the formula I mentioned above, n is 2, then $R^4$ can be straight-chain alkylene having 1 to 10 C atoms. Examples which may be mentioned are methylene, ethylene, trimethylene, tetramethylene, pentamethylene, hexamethylene, octamethylene or decamethylene, ethylene being preferred. Examples of straight-chain alkylene groups which have 1 to 10 C atoms and which are substituted by at least one, expediently 1 to 3, and preferably 1 or 2, alkyl groups having 1 to 4 C atoms, as likewise mentioned in the case of $R^4$, are 1-methyl- 1,2-ethanediyl, 1-ethyl- 1,2-ethanediyl, 2,2-dimethyl- 1,3-propanediyl or 2-methyl- 2-n-butyl- 1,3-propanediyl.

Examples of straight-chain alkylene groups which have 2 to 10 C atoms and which are interrupted by at least one —S— or —O—, as mentioned in the case of $R^4$, can have the formulae —$CH_2$—$CH_2$—S—$CH_2$—$CH_2$—, —$CH_2$—$CH_2$—O—$CH_2$—$CH_2$—, —$CH_2$—$CH_2$—O—$CH_2$—$CH_2$—O—$CH_2$—$CH_2$— or —$CH2$—$CH_2$—O—$CH_2$—$CH_2$—O—$CH_2$—$CH_2$—O— $CH_2$—$CH_2$—.

If $R^4$ has the meaning of alkenylene having 2 to 10 C atoms, then examples which may be mentioned are vinylene, methylvinylene, octenylethylene or 2-butene-1,4-diyl.

If $R^4$ has the meaning of a bivalent heterocycle having 5 to 6 ring members with 1 to 4 nitrogen atoms, or of a bivalent heterocycle having 5 to 6 ring members with one or two nitrogen atoms and one further hetero atom from the series comprising O or S, or of the abovementioned bivalent heterocycles which are fused to a benzo radical, and/or the abovementioned bivalent heterocycles which are substituted on one or two of the C atoms by =S or $C_1$–$C_4$alkyl, then examples which may be mentioned are:

If n is 3, then $R^4$ is a group of the formula

The expedient compounds of the formula I mentioned above include those in which n is 1 and $R^4$ is a group in which n is 2 and $R^4$ is a group in which
$R^8$ and $R^9$, independently of one another, are $C_1$–$C_{12}$alkyl, phenyl, a group —$OR^{10}$, —$SR^{11}$ or $$-\underset{R^{11}}{\underset{|}{N}}-R^{12},$$

and $R^{10}$ is $C_1$–$C_{12}$alkyl, $C_5$–$C_8$cycloalkyl, mono-, di- or tri-($C_1$–$C_4$alkyl)-substituted $C_5$–$C_8$cycloalkyl, allyl, phenyl or benzyl, and $R^{11}$ and $R^{12}$ which are identical or different, are —H, $C_1$–$C_{12}$alkyl, $C_5$–$C_8$cycloalkyl, mono-, di- or tri-($C_1$–$C_4$)-substituted $C_5$–$C_8$cycloalkyl, allyl, benzyl, $C_2$–$C_3$alkyl, which is substituted in the 2- or 3-position by —OH, by $C_1$–$C_4$alkoxy or by di($C_1$–$C_4$alkyl)amino, or are the group $$-\underset{R^{11}}{\underset{|}{N}}-R^{12},$$

1-pyrrolidyl, 1-piperidyl, 4-morpholinyl or 1-hexahydroazepinyl.

The preferred compounds of the formula I mentioned above include those in which n is 1 and $R^4$ is a group or in which n is 2 and $R^4$ is a group in which
$R^8$ and $R^9$, independently of one another, are $C_1$–$C_4$alkyl, phenyl, a group —$OR^{10}$, —$SR^{10}$ or $$-\underset{R^{12}}{\underset{|}{N}}-R^{11},$$

in which $R^{10}$ is $C_1$–$C_{10}$alkyl, cyclohexyl, mono-, di- or tri-($C_1$–$C_4$alkyl)-substituted cyclohexyl, allyl, phenyl or benzyl, and $R^{11}$ and $R^{12}$ are identical or different and are —H, $C_1$–$C_{12}$alkyl, cyclohexyl, mono-, di- or tri-($C_1$–$C_4$alkyl)-substituted cyclohexyl, allyl, benzyl, $C_2$–$C_3$alkyl, which is substituted in the 2- or 3-position by —OH, by methoxy, by ethoxy, by dimethylamino or diethylamino, or $R^{11}$ and $R^{12}$ together with the N atom linking them are a morpholino group. $R^8$ and $R^9$ are preferably identical.

The present invention also comprises compositions containing a) an organic material and b) at least one compound of the general formula I $$\left[ \begin{array}{c} R^1-O \\ R^2-Q \end{array} \underset{Y-T}{\overset{X}{\underset{\diagup}{P}}} \right]_n R^4, \quad (I)$$

in which n is 1, 2 or 3 and in which X is oxygen or sulfur, T has the meaning of —S—, —S—S—, —S—S—S—, —S—S—S—S—, —S—S—S—S—S—, $$-\underset{O}{\overset{O}{\underset{\parallel}{S}}}-, \quad -\underset{O}{\overset{O}{\underset{\parallel}{S}}}- \quad \text{or} \quad -\underset{O}{\overset{O}{\underset{\parallel}{S}}}-\underset{O}{\overset{}{\underset{\parallel}{S}}}$$

and Y has the meaning of $$-\underset{R^3}{\underset{|}{C}}-CH_2-$$
$$\overset{|}{O-Z}$$

in which Z has the meaning of —H, —$COR^{13}$, —$COOR^{13}$ or —$CONHR^{13}$, and Q has the meaning of oxygen or —NR⁰—, and R¹, R², R⁰ and R¹³ are identical or different and are an alkyl group having 1 to 18 C atoms, an alkenyl group having 2 to 18 C atoms, a phenyl or naphthyl group, a phenyl or naphthyl group each of which is substituted by at least one C₁–C₉alkyl group, or are a phenylalkyl group having 7 to 9 C atoms, a cycloalkyl group having 5 to 12 ring C atoms or a cycloalkyl group having 5 to 12 ring C atoms which is substituted by at least one alkyl group having 1 to 4 C atoms, or R⁰ is —H, or R¹ and R² together are a straight-chain alkylene group having 2 to 10 C atoms, a straight-chain alkylene group having 2 to 10 C atoms which is substituted by at least one alkyl group having 1 to 8 C atoms or by at least one group —CH₂—O—C₁–C₁₂alkyl or —CH₂—S—C₁–C₁₂alkyl, or R¹ and R² together are a group of the formula

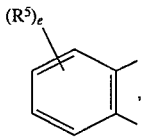

in which R⁵ is an alkyl group having 1 to 4 C atoms and e is a number 0, 1 or 2, or R¹ and R² together are a group of the formula

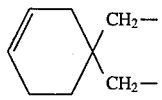

R³ has the meaning of —H, alkyl having 1 to 4 C atoms, phenyl, —CH₂—S—R⁴', in which R⁴' is as defined below, or is phenyl or phenyl substituted by at least one alkyl group having 1 to 4 C atoms, and, if n is 1, R⁴ has the meaning of R⁴' in which R⁴' is —H, an alkyl group having 1 to 18 C atoms, an alkenyl group having 2 to 18 C atoms, a phenyl or naphthyl group, a phenyl or naphthyl group which is substituted by at least one C₁–C₉alkyl group, or is a phenylalkyl group having 7 to 9 C atoms, pinan- 10-yl, an alkyl group having 1 to 18 C atoms which is substituted by at least one OH group, an alkyl group having 2 to 18 C atoms which is interrupted by at least one —S— or —O—, an alkyl group having 3 to 18 C atoms which is substituted by at least one OH group and interrupted by at least one —S— or —O—, a group of the formula —R⁶—COOR⁷ in which R⁶ is an alkylene group having 1 to 6 C atoms and R⁷ is an alkyl group having 1 to 12 C atoms, a cycloalkyl group having 5 to 12 ring C atoms, a cycloalkyl group having 5 to 12 ring C atoms which is substituted by at least one alkyl group having 1 to 4 C atoms, or is a cycloalkyl group having 5 to 12 ring C atoms which is interrupted by at least one —O— or —S—, or is a cycloalkyl group having 5 to 12 ring C atoms which is substituted by at least one alkyl group having 1 to 4 C atoms and interrupted by at least one —O— or —S—, or R⁴' is a group of the formula

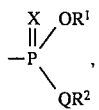

in which X is oxygen or sulfur and Q, R¹ and R² are as defined above, or R⁴' is a heterocycle having 5 to 6 ring members with 1 to 3 members front the series comprising —NH—, —N=,

or —N(C₁–C₄alkyl)—, or a heterocycle having 5 to 6 ring members with one or two members from the series comprising —NH—, —N=,

or —N(C₁–C₄alkyl)— and one further hetero atom from the series comprising O or S, or the abovementioned heterocycles which are fused to a benzo radical, or the abovementioned heterocycles which are substituted on one or two of the C atoms by =S and/or C₁C₄alkyl, or R⁴' has the meaning of

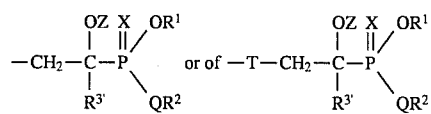

in which T and Z are as defined above, X is oxygen or sulfur, R³' is —H, alkyl having 1 to 4 C atoms, phenyl or phenyl which is substituted by at least one alkyl group having 1 to 9 C atoms, and Q, R¹ and R² are as defined above, or R⁴ has the meaning of

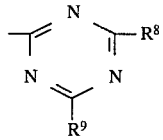

in which R⁸ mad R⁹, independently of one another, are C₁–C₁₈alkyl, phenyl, phenyl which is mono-, di- or tri-C₁–C₄alkyl-substituted, or am a group —OR¹⁰, —SR¹⁰ or

in which R¹⁰ is C₁–C₁₈alkyl, C₅–C₁₂cycloalkyl, C₅–C₁₂cycloalkyl which is mono-, di- or tri-C₁–C₄alkyl-substituted, or is C₃–C₆alkenyl, phenyl, phenyl which is mono-, di- or tri-C₁–C₄alkyl-substituted, or is C₇–C₉phenylalkyl or C₇–C₉phenylalkyl which is mono-, di- or tri-C₁–C₄alkyl-substituted on the phenyl, and R¹¹ and R¹² which are identical or different are —H, C₁–C₁₈alkyl, C₅–C₁₂cycloalkyl, C₅–C₁₂cycloalkyl which is mono-, di- or tri-C₁–C₄alkyl-substituted, or are C₁–C₆alkenyl, C₇–C₉phenylalkyl, C₇–C₉phenylalkyl which is mono-, di- or tri-C₁–C₄alkyl-substituted on the phenyl, or are C₂–C₄alkyl which is substituted by —OH, by C₁–C₈alkoxy or by di(C₁–C₄alkyl)amino, or R¹¹ and R¹² together with the nitrogen atom linking them are a 5- to 7-membered heterocycle, or, if n is 2, R⁴ is: straight-chain alkylene having 1 to 12 C atoms or alkenylene having 2 to 10 C atoms or straight-chain alkylene having 1 to 10 C atoms which is substituted by at least one alkyl group having 1 to 4 C atoms, or straight-chain alkylene having 2 to 10 C atoms which is interrupted by —S— or —O—, or alkylene having 2 to 10 C atoms which is substituted by at least one alkyl group having 1 to 4 C atoms and interrupted by —S— or —O—, or R⁴ has the meaning of a bivalent heterocycle having 5 to 6 ring members with 1 to 3 nitrogen atoms, or of a bivalent heterocycle with 5 to 6 ring members with one nitrogen atom and one further hetero atom from the series comprising O or S, or of the abovementioned bivalent heterocycles which are fused to a benzo radical, or of the abovementioned bivalent heterocycles which are substituted by =S or $C_1$–$C_4$alkyl on one or two of the C atoms, or, $R^4$ has the meaning of

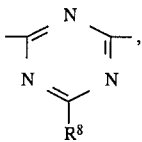

in which $R^8$ is as defined above, or,
if n is 3,
$R^4$ is a group of the formula

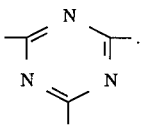

Expedient and preferred compositions are obtained, for example, by selecting the components b), compounds of the general formula I, as described above, in their expedient and preferred embodiments.

Other expedient embodiments are obtained by selecting the organic material a).

Suitable organic material can be seen, for example, from the list below.

1. Polymers of mono- and diolefins, for example polypropylene, polyisobutylene, polybut-1-ene, polymethylpent-1-ene, polyisoprene or polybutadiene, and also polymers of cycloolefins, for example of cyclopentene or norbornene; further polyethylene (which can be linear or crosslinked), for example high-density polyethylene (HDPE), low-density polyethylene (LDPE), linear low-density polyethylene (LLDPE).

2. Mixtures of polymers mentioned under 1), for example mixtures of polypropylene with polyisobutylene, polypropylene with polyethylene (for example PP/HDPE, PP/LDPE) and mixtures of various polyethylene types (for example LDPE/HDPE).

3. Copolymers of mono- and diolefins with one another or with other vinyl monomers, for example ethylene/propylene copolymers, linear low-density polyethylene (LLDPE) and mixtures of the latter with low-density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and their salts (ionomers), and also terpolymers of ethylene with propylene and a diene, for example hexadiene, dicyclopentadiene or ethylidenenorbornene; furthermore mixtures of such copolymers with one another and with polymers mentioned under 1), for example polyproplene and ethylene/propylene copolymers, LDPE with ethylene/vinyl acetate copolymers, LDPE with ethylene/acrylic acid copolymers, LLDPE with ethylene/vinyl acetate copolymers and LLDPE with ethylene/acrylic acid copolymers.

3a. Hydrocarbon resins (for example $C_5$–$C_9$) including hydrogenated modifications thereof (for example tackifier resins).

4. Polystyrene, poly(p-methylstyrene), poly(α-methylstyrene).

5. Copolymers of styrene or a-methylstryene with dienes or acrylic derivatives, for example styrene/butadiene, styrene/acrylonitrile, stryene/alkyl methacrylate, styrene/butadiene/alkyl acrylate, styrene/maleic anhydride, styrene/acrylonitrile/methyl acrylate; mixtures of high impact strength made of styrene copolymers and one other polymer, for example a polyacrylate, a diene polymer or an ethylene/propylene/diene terpolymer; and also block copolymers of styrene, for example styrene/butadiene/styrene, styrene/isoprene/styrene, styrene/ethylene with butylene/styrene or styrene/ethylene with propylene/stryene.

6. Graft copolymers of styrene or a-methylstyrene, for example styrene on polybutadiene, styrene on polybutadiene/styrene copolymers or on polybutadiene/acrylonitrile copolymers, styrene and acrylonitrile (or methacrylonitrile) on polybutadiene; styrene, acrylonitrile and methyl methacrylate on polybutadiene; stryene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and their mixtures with the copolymers mentioned under 5), as are known as, for example, so-called ABS, MBS, ASA or AES polymers.

7. Halogen-containing polymers, for example polychloroprene, chlorinated rubber, chlorinated or chlorosulfonated polyethylene, epichlorohydrin homopolymers and copolymers, in particular polymers of halogen-containing vinyl compounds, for example polyvinyl chloride, polyvinylidene chloride, polyvinyl fluoride, polyvinylidene fluoride; and their copolymers, such as vinyl chloride/vinylidene chloride, vinyl chloride/vinyl acetate or vinylidene chloride/vinyl acetate.

8. Polymers which are derived from α,β-unsaturated acids and their derivatives, such as polyacrylates and polymethacrylates, polyacrylamides and polyacrylonitriles.

9. Copolymers of the monomers mentioned under 8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers, or acrylonitrile/alkyl methacrylate/butadiene terpolymers.

10. Polymers which are derived from unsaturated alcohols and amines or of their acyl derivatives or acetals, for example polyvinyl alcohol, polyvinyl acetate, polyvinyl stearate, polyvinyl benzoate, polyvinyl maleate, polyvinyl butyral, polyallyl phthalate, polyallylmelamine; and their copolymers with the olefins mentioned in item 1.

11. Homo- and copolymers of cyclic ethers, for example polyalkylene glycols, polyethylene oxide, polypropylene oxide, or their copolymers with bisglycidyl ethers.

12. Polyacetals, for example polyoxymethylene, and those polyoxymethylenes which contain comonomers, for example ethylene oxide; polyacetals which are modified with thermoplastic polyurethanes, acrylates or MBS.

13. Polyphenylene oxides and polyphenylene sulfides, and their mixtures with styrene polymers or polyamides.

14. Polyurethanes which are derived from polyethers, polyesters and polybutadienes with terminal hydroxyl groups on the one hand, and aliphatic or aromatic polyisocyanates on the other hand, and their precursors.

15. Polyamides and copolyamides which are derived from diamines and dicarboxylic acids and/or from aminocarboxylic acids or the corresponding lactams, for example polyamide 4, polyamide 6, polyamide 6/6, 6/10, 6/9, 6/12, 4/6, polyamide 11, polyamide 12, aromatic polyamides starting from m-xylene, diamine and adipic acid; polyamides prepared from hexamethylenediamine and iso- and/or terephthalic acid and, if desired, an elastomer as modifier, for example poly-2,4,4-trimethylhexamethyleneterephthalamide, poly-m-phenylene-isophthalamide. Block copolymers of the polyamides mentioned above with polyolefins, olefin copolymers, ionomers or chemically bonded or grafted elastomers; or with polyethers, for example polyethylene glycol, polypropylene glycol or polytetramethylene glycol. Furthermore EPDM- or ABS-modified polyamides or copolyamides; and polyamides condensed during processing ("RIM polyamide systems").

16. Polyureas, polyimides, polyamide-imides and polybenzimidazoles.

17. Polyesters which are derived from dicarboxylic acids and dialcohols and/or from hydroxycarboxylic acids or the corresponding lactones, for example polyethylene terephthalate, polybutylene terephthalate, poly-1,4-dimethylolcyclohexane terephthalate, polyhydroxybenzoates, and block polyethers/esters which are derived from polyethers having terminal hydroxyl groups; furthermore polycarbonates or MBS-modified polyesters.

18. Polycarbonates and polyester carbonates.

19. Polysulfones, polyether sulfones and polyether ketones.

20. Crosslinked polymers which are derived from aldehydes on the one hand and phenols, urea or melamine on the other hand, for example phenol/formaldehyde, urea/formaldehyde and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also their halogen-containing modifications with low flammability.

23. Crosslinkable acrylic resins which are derived from substituted acrylic esters, for example epoxy-acrylates, urethane-acrylates or polyester-acrylates.

24. Alkyd resins, polyester resins and acrylate resins, all of which are crosslinked with melamine resins, urea resins, polyisocyanates or epoxide resins.

25. Crosslinked epoxide resins which are derived from polyepoxides, for example from bis-glycidyl ethers or from cycloaliphatic diepoxides.

26. Natural polymers, for example cellulose, natural rubber, gelatine, and their derivatives which have been chemically modified to give homologous polymers, for example cellulose acetates, cellulose propionates and cellulose butyrates, or the cellulose ethers, for example methyl cellulose; and also colophonium resins and derivatives.

27. Mixtures (polyblends) of the previously mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

28. Natural and synthetic organic substances which represent pure monomeric compounds or mixtures of these, for example mineral oil, animal or vegetable fats, oils and waxes, or oils, waxes and fats on the basis of synthetic esters (for example phthalates, adipates, phosphates or trimellitates), and mixtures of synthetic esters with mineral oils in any desired ratio by weight, as are used, for example, as spinning preparations, and their aqueous emulsions.

29. Aqueous emulsions of natural or synthetic rubbers, for example natural rubber latex or latices of carboxylated styrene/butadiene copolymers.

The compounds of the formula I according to the invention and any further additions are incorporated into the organic material by methods known per se. For example, this can be carried out by mixing in the products according to the invention and, if desired, further additives using methods which are conventional in the art, before or during shaping, or, alternatively, by applying the dissolved or dispersed compounds onto the polymer, followed, if desired, by evaporating the solvent. It is also possible to add the products according to the invention to the materials to be stabilised in the form of a master batch which contains these products in a concentration of, for example, 2.5 to 25% by weight. The products according to the invention can also be added before or during polymerisation or before crosslinking.

The compounds of the formula I can expediently be incorporated using the following methods:

as emulsion or dispersion (for example to latices or emulsion polymers)

as a dry mixture during the mixing of additional components or polymer mixtures direct addition into the processing apparatus (for example extruder, internal mixture etc.)

as a solution or melt.

The compounds of the formula I can be employed in the organic material in amounts of, for example, 0.01 to 10% by weight, expediently 0.1 to 5% by weight and preferably 0.1 to 3% by weight, based on the organic material.

The materials which have been stabilised in this manner can be used in a large number of ways, for example as foils, fibres, ribbons, moulding compositions, profiles, or as binders for varnishes, adhesives or putties.

The compounds of the formula I are valuable additives in organic materials.

In addition to the compounds of the formula I, the organic materials mentioned above and, in particular, the synthetic polymers, can contain other additives. Examples of additional additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-di-cyclopentyl-4-methylphenol, 2-(a-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butyl-hydroquinone, 2,5-di-tert-amyl-hydroquinone, 2,6-diphenyl-4-octadecyloxyphenol.

1.3. Hydroxylated thiodiphenyl ethers, for example 2,2'-thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

1.4 Alkylidene-bisphenols, for example 2,2'-methylene-bis-(6-tert-butyl-4-methylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-ten-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)butane, 2,6-bis-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)butyrate], bis-(3-tert-butyl-4-hydroxy-5-methylphenyl)dicyclopentadiene, bis-[2-(3'-tert-butyl-2'-hydroxy-5'-methylbenzyl)-6-tert-butyl-4-methylphenyl]terephthalate.

1.5 Benzyl compounds, for example 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-ten-butyl-4-hydroxybenzylmercaptoacetate, bis-(4-ten-butyl-3-hydroxy-2,6-dimethylbenzyl) dithiolterephthalate, 1,3,5-tris-(3,5-di-ten-butyl-4-hydroxybenzyl) isocyanurate, 1,3,5-tris-(4-ten-butyl-3-hydroxy-2,6-dimethylbenzyl) isocyanurate, dioctadecyl 3,5-di-tert-butyl-4-hydroxybenzylphosphonate, the calcium salt of monoethyl 3,5-di-tert-butyl-4-hydroxybenzylphosphonate, 1,3,5-tris-(3,5-dicyclohexyl-4-hydroxybenzyl)isocyanurate.

1.6. Acylaminophenols, for example 4-hydroxylauranilide, 4-hydroxystearanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris-hydroxyethyl isocyanurate, N,N'-bis-hydroxyethyl-oxalic diamide.

1.8. Esters of β-(5-tert-butyl-4-hydroxy-3-methylphenyl)propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris-hydroxyethyl isocyanurate, N,N'-bis-hydroxyethyl-oxalic diamide.

1.9. Esters of β-(3,5-dicyclohexyl-4-hydroxyphenyl)propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris-hydroxyethyl isocyanurate, N,N'-bis-hydroxyethyl-oxalic diamide.

1.10. Amides of β-(3,5-di-tert-butyl-4-hydroxyphyenyl)propionic acid, for example N,N'-bis-(3,5-di-tert-butyl-4-hydroxyphenylpropionyl)hexamethylenediamine, N,N'-bis-(3,5-di-tert-butyl-4-hydroxyphenylpropionyl)trimethylenediamine, N,N'-bis-(3,5-di-tert-butyl-4-hydroxyphenylpropionyl)hydrazine.

2. UV-absorbers and light-stabilisers 2.1. 2-(2'-Hydroxyphgnyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl or 3',5'-bis-(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy or 2'-hydroxy-4,4'-dimethoxy derivative.

2.3. Esters of substituted or unsubstituted benzoic acids, for example 4-tert-butylphenyl salicylate, phenyl salicylate, octylphenyl salicylate, dibenzoylresorcinol, bis-(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate.

2.4. Acrylates, for example ethyl α-cyano-β,β-diphenylacrylate or isooctyl α-cyano-β,β-diphenylacrylate, methyl α-carbomethoxycinnamate, methyl α-cyano-β-methyl-p-methoxycinnamate or butyl α-cyano-β-methyl-p-methoxycinnamate, methyl α-carbomethoxy-p-methoxycinnamate or N-(β-carbomethoxy-β-cyanovinyl)-2-methylindoline.

2.5. Nickel compounds, for example nickel complexes of 2,2'-thio-bis-[4-(1,1,3,3-tetramethylbutyl)-phenol], such as the 1: 1 or 1:2 complex, if desired having additional ligands such as n-butylamine, triethanolamine or N-cyclohexyl-diethanolamine, nickel dibutyldithiocarbamate, nickel salts of the monoalkyl esters of 4-hydroxy-3,5-di-ten-butylbenzylphosphonic acid, such as the methyl or ethyl esters, nickel complexes of ketoximes, such as of 2-hydroxy-4-methylphenyl undecyl ketoxime, nickel complexes of 1-phenyl-4-lauroyl-5-hydroxypyrazole, if desired with additional ligands.

2.6 Sterically hindered amines, for example bis-(2,2,6,6-tetramethylpiperidyl) sebacate, bis-(1,2,2,6,6-pentamethylpiperidyl) sebacate, bis( 1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis-(2,2,6,6-tetramethyl-4-piperidyl)-hexamethylenediamine and 4-tert-octyl-amino-2,6-dichloro- 1,3,5-s-triazine, tris-(2,2,6,6-tetramethyl-4-piperidyl) nitrilotriacetate, tetrakis-(2,2,6,6-tetramethyl-4-piperidyl) 1,2,3,4-butanetetraoate, 1,1'-(1,2-ethanediyl)-bis-(3,3,5,5-tetramethylpiperazinone).

2.7. Oxalic acid diamides, for example 4,4'-dioctyloxyoxanilide, 2,2'-dioctyloxy-5,5'-di-tert-butyl-oxanilide, 2,2'-didodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyl-oxanilide and its mixture with 2-ethoxy-2'-ethyl-5,4'-di-tert-butyl-oxanilide, or mixtures of o- and p-methoxy- and also of o- and p-ethoxy-disubstituted oxanilides.

2.8.2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalic diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylideneoxalic dihydrazide.

4. Phosphites and phosphonites, for example triphenyl phosphite, diphenyl alkyl phosphites, phenyl dialkyl phosphites, tris-(nonylphenyl) phosphite, trilauryl phosphite, trioctadecyl phosphite, distearyl pentaerythritol diphosphite, tris-(2,4-di-tert-butylphenyl) phosphite, diisodecyl pentaerythritol diphosphite, bis-(2,4-di-tert-butylphenyl) pentaerythritol diphosphite, tristearyl sorbitol triphosphite, tetrakis-(2,4-di-tert-butylphenyl) 4,4'-biphenylenediphosphonite, 3,9-bis-(2,4-di-tert-butylphenoxy)-2,4,8,10-tetraoxa-3,9-diphosphaspiro[5.5]undecane.

5. Peroxide-destroying compounds, for example esters of g-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide and penyterythritol tetrakis-(β-dodecylmercapto)propionate.

6. Polyamide stabilisers, for example copper salts in combination with iodides and/or phosphorus compounds and divalent manganese salts.

7. Basic costabilisers, for example melamine, polyvinylpyrrolidone, dicyandiamide, triallyl cyanurate, urea derivatives, hydrazine derivatives, amines, polyamides, polyurethanes, alkali metal salts or alkaline earth metal salts of higher fatty acids, for example Ca stearate, Zn stearate, Mg stearate, Na ricinoleate and K palmirate, antimony pyrocatecholate or tin pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and metal hydroxides, carbon black, graphite.

10. Further additives, for example plasticisers, lubricants, emulsifiers, pigments, fluorescent whiteners, flameproofing agents, antistatic agents, foaming agents.

Preferred organic material is mentioned in the above list under item 28. These include, in particular, the functional liquids which include, for example, the lubricants, the hydraulic liquids and the metal-working liquids.

Examples of lubricants which may be mentioned are the lubricating oils for combustion engines, the hydraulic oils, the compressor oils and the so-called industrial lubricants which embrace, for example, the groups of the turbine oils, for both steam and gas turbines.

Lubricating oils for combustion engines comprise, in particular, the lubricating oils which actuate the lubricating circuit of a combustion engine from the crankcase or dry sump. By combustion engines there are meant, for example, hoisting-piston motors or rotary-piston motors with compression ignition or spark ignition (diesel or Otto principle).

The lubricants, hydraulic liquids and metal-working liquids in question are based, for example, on mineral and synthetic oils and of oils derived from sources of the organic environment, or mixtures of these. The lubricants are known to those skilled in the art and described in the specialist literature, for example in Dieter Klamann "Schmierstoffe und verwandte Produkte" [Lubricants and Related Products] (Verlag Chemie, Weinheim, 1982), in Schewe-Kobek "Das Schiermittel-Taschenbuch" [Lubricant Guide](Dr. Alfred H üthig-Verlag, Heidelberg, 1974) and in "Ullmanns Enzyklop ädie der technischen Chemie" [Ullmann's Encyclopaedia of Industrial Chemistry], Vol 13, pages 85–94 (Verlag Chemie, Weinheim, 1977).

The lubricants are, in particular, oils. They also embrace fats, for example those based on a mineral oil.

The mineral oils are based, in particular, on hydrocarbon compounds.

Examples of synthetic lubricants comprise lubricants on the basis of the aliphatic or aromatic carboxylic esters, the polymeric esters, the polyalkylene oxides, the phosphoric esters, the poly-α-olefins or the silicones, of a diester of a dibasic acid with a monohydric alcohol, for example dioctyl sebacate or dinonyl adipate, of a triester of trimethylolpropane with a monobasic acid or with a mixture of such acids, for example trimethylolpropane tripelargonate, trimethylolpropane tricaprylate or their mixtures, of a tetraester of pentaerythritol with a monobasic acid or with a mixture of such acids, for example pentaerythritol tetracaprylate, or of a complex ester of monobasic and dibasic acids with polyhydric alcohols, for a complex ester of trimethylolpropane with caprylic and sebacic acid or of a mixture thereof. Besides mineral oils, examples of particularly suitable substances are poly-α-olefins, lubricants on an ester base, phosphates, glycols, polyglycols and polyalkylene glycols, and their mixtures with water.

Hydraulic oils, for example, but also lubricating oils and lubricating fats can be based on animal and vegetable substances and examples which may be mentioned are animal tallows, sperm oil, fish oil, bone oil, palm-kernel oil, rape-seed oil, linseed oil, rape oil, soya oil, coconut oil, nut oil, and their modified forms, such as epoxidised and sulfurised forms.

In addition, the lubricants can contain other additives which are added to further improve the basic properties of lubricants; they include: antioxidants, metal passivators, rust inhibitors, viscosity index improvers, pour-point depressants, dispersants, detergents, high-pressure additives and anti-wear additives.

A series of such compounds can be seen, for example, from the above list "1. Antioxidants", in particular items 1.1 to 1.10. In addition, the examples of further additives to be mentioned are:

Example of amine antioxidants:
N,N'-diisopropyl-p-phenylenediamine, N,N'-di-sec-butyl-p-phenylenediamine,
N,N'-bis(1,4-dimethylpentyl)-p-phenylenediamine,
N,N'-bis(1-ethyl-3-methylpentyl)-p-phenylenediamine,
N,N'-bis(1-methylheptyl)-p-phenylenediamine, N,N'-dicyclohexyl-p-phenylenediamine,
N,N'-diphenyl-p-phenylenediamine, N,N'-di(2-naphthyl)-p-phenylenediamine,
N-isopropyl-N'-phenyl-p-phenylenediamine,
N-(1,3-dimethylbutyl)-N'-phenyl-p-phenylenediamine,
N-(1-methylheptyl)-N'-phenyl-p-phenylenediamine,
N-cyclohexyl-N'-phenyl-p-phenylenediamine, 4-(p-toluenesulfonamido)diphenylamine,
N,N'-dimethyl-N,N'-di-sec-butyl-p-phenylenediamine, diphenylamine,
N-allyldiphenylamine, 4-isopropoxydiphenylamine, N-phenyl-1-naphthylamine,
N-phenyl-2-naphthylamine, octylated diphenylamine, for example
p,p'-di-tert-octyldiphenylamine, 4-n-butylaminophenol, 4-butyrylaminophenol,
4-nonanoylaminophenol, 4-dodecanoylaminophenol, 4-octadecanoylaminophenol,
di-(4-methoxyphenyl)amine, 2,6-di-tert-butyl-4-dimethylaminomethylphenol,
2,4'-diaminodiphenylmethane, 4,4'-diaminodiphenylmethane,
N,N,N',N'-tetramethyl-4,4'-diaminodiphenylmethane,
1,2-di-[(2-methylphenyl)amino]ethane, 1,2-di-(phenylamino)propane, (o-tolyl)biguanide,
di-[4-(1',3'-dimethylbutyl)phenyl]amine, tert-octylated N-phenyl-1-naphthylamine,
mixture of mono- and dialkylated tert-butyl- and tert-octyldiphenylamines,
2,3-dihydro-3,3-dimethyl-4H-1,4-benzothiazine, phenothiazine, N-allylphenothiazine.

Examples of further antioxidants:
Aliphatic or aromatic phosphites, esters of thiodipropionic acid or of thiodiacetic acid, or salts of dithiocarbamic or dithiophosphoric acid.

Examples of metal passivators, for example copper, are:
Triazoles, benzotriazoles and their derivatives, tolutriazoles and their derivatives,
2-mercaptobenzothiazole, 2-mercaptobenzotriazole, 2,5-dimercaptobenzotriazole,
2,5-dimercaptothiadiazole, 5,5'-methylenebisbenzotriazole,
4,5,6,7-tetrahydrobenzotriazole, salicylidene-propylenediamine, salicylaminoguanidine and its salts.

Examples of rust inhibitors are:
a) Organic acids, their esters, metal salts and anhydrides, for example: N-oleoyl-sarcosine, sorbitan monooleate, lead naphthenate, alkenylsuccinic anhydride, for example dodecenylsuccinic anhydride, partial esters and partial amides of alkenylsuccinic acid, and 4-nonylphenoxyacetic acid.
b) Nitrogen-containing compounds, for example: I. Primary, secondary or tertiary aliphatic or cycloaliphatic amines and amine salts of organic and inorganic acids, for example oil-soluble alkylammonium carboxylates.
II. Heterocyclic compounds, for example: substituted imidazolines and oxazolines.
c) Phosphorus-containing compounds, for example: amine salts of partial esters of phosphoric acid or of phosphonic acid, and zinc dialkyldithiophosphates.
d) Sulfur-containing compounds, for example: barium dinonylnaphthalinesulfonates, calciumpetroleum sulfonates.

Examples of viscosity-index improvers are:
Polyacrylates, polymethacrylates, vinylpyrrolidione/methacrylate copolymers, polyvinylpyrrolidones, polybutenes, olefin-copolymers, stryrene/acrylate copolymers, polyethers.

Examples of pour-point depressants are:
Polymethacrylate, alkylated napththaline derivatives.

Examples of dispersants/suffactants/detergents are:
Polybutenylsuccinamides or polybutenylsuccinimides, polybutentylphosphonic acid derivatives, basic magnesium sulfonates, magnesium phenolates, calcium sulfonates, calcium phenolates, barium sulfonates and barium phenolates.

Examples of high: pressure additives/anti-wear additives are:
Sulfur- and/or phosphorus- and/or halogen-containing compounds, such as sulfurised vegetable oils, zinc dialkyldithiophosphates, tritolyl phosphate, chlorinated paraffins, alkyl disulfides, alkyl trisulfides, aryl disulfides and aryl trisulfides, triphenyl phosphorothionates, diethanolaminomethyltolyltriazole, di(2-ethylhexyl)aminomethyltolyltriazole.

The organic materials contain, for example, 0.01 to 10% by weight, expediently 0.05 to 5% by weight, preferably 0.05 to 3% by weight, and, in particular, 0.1 to 2% by weight, of a total of at least one compound of the formula I, as mentioned above.

In the case of thermoplastics and elastomers, such compositions according to the invention have outstanding working properties and application properties, and, accordingly, the compounds of the formula I according to the invention can be classified as working additives and application additives for thermoplastics and elastomers.

In functional liquids, such as lubricants, the compounds of the formula I according to the invention have the properties of a multifunctional additive and improve the high-pressure and abrasion properties in an outstanding manner. Their effect on reducing abrasion and the corrosion/rust-inhibiting effect must be particularly emphasised.

The present invention also embraces the use of the compounds of the formula I, as mentioned above, in organic materials. Expedient and preferred uses can be derived accordingly from expedient and preferred compounds of the formula I and from organic materials which are termed expedient and preferred.

The compounds of the formula I in which Z is —H, of the present invention, can be obtained by the process according to the invention, which comprises reacting a compound of the general formula II

in which X, Q, $R^1$ and $R^2$ are as defined given further above, with a compound of the general formula III

in which $R^3$ likewise is as defined further above and Hal has the meaning of I, Br or preferably Cl, in a first reaction step, to give a compound of the general formula IV

in which X, Q, $R^1$, $R^2$, $R^3$ and Hal are as defined above, and, in a second reaction step, reacting the compound of the general formula IV with a compound of the general formula $$[MS \!\!\mid_{\overline{n}} R^4 \quad (V)$$

or with a compound of the general formula Va $$M-S-M \quad (Va)$$

or with a compound of the formula Vb $$M\!+\!S\!\mid_{\overline{q}} M \quad (Vb)$$

in which q is a number 2, 3, 4 or 5, in which $R^4$ and n are as defined further above and M has the meaning of alkali metal or —H. If M in compounds of the formulae V, Va or Vb has the meaning of —H, it is also possible to use, if desired, a tertiary amine, for example $(C_2H_5)_3N$ or $(nC_4H_9)_3N$ as the condensing agent.

Compounds of the formula I in which Z has the meaning of —$COR^{13}$, —$COOR^{13}$ or —$CONHR^3$ can be prepared in a manner known per se, for example from compounds of the formula I in which Z has the meaning of —H, by acylation using acylating agents, by reaction with corresponding anhydrides, acid chlorides, carbonic acid chlorides or by addition onto corresponding isocyanates. For example, the process can also be carried out with the aid of the phase-transfer technique.

As an alkali metal, N can be, for example, Li, Na, K, Rb or Cs, preferably Na or K, and, in particular, Na.

The use of compounds of the formulae II, III, IV and V in which the substituents $R^1$, $R^2$, $R^3$ and $R^4$ are expedient or preferred embodiments, lead to expedient or preferred processes.

Expedient processes according to the invention are those wherein the first reaction step, which leads to compounds of the formula IV, is carried out in the presence of a basic catalyst.

Examples of suitable basic catalysts for this reaction step are alkali metal hydroxides, such as sodium hydroxide or potassium hydroxide, alkali metal alcoholates, such as sodium methylate, sodium ethylate, sodium propylate, potassium methylate, potassium ethylate or potassium propylate. It is expedient to use sodium hydroxide, potassium hydroxide, sodium methylate or sodium ethylate as the catalyst.

The amount of catalyst is not critical; it is expedient to employ 0.001 to 20% by weight, preferably 0.01 to 10% by weight, of the catalyst based on the compound of the formula II in the first reaction step.

The second reaction step is advantageously carried out using stoichiometric amounts of an alkali metal mercaptide $M-SR^4$ or $M-S-M$ or $M-(S)_q-M$ in which M and $R^4$ are defined as mentioned and q is 2, 3, 4 or 5.

The second reaction step, the thiolyric exchange of halogen in compounds of the formula III, can, for example, also be carried out using the corresponding SH compounds, it being possible to use stoichiometric amounts of tertiary amines.

Suitable tertiary amines have the formula

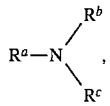

in which $R^a$, $R^b$ and $R^c$, independently of one another, are linear or branched $C_1$–$C_8$alkyl radicals, $C_3$–$C_8$alkenyl radicals, cycloalkyl having 5 to 12 ring C atoms, phenyl or $C_1$–$C_4$alkyl-substituted phenyl, and it is furthermore possible to use, for example, pyridine derivatives and other heterocyclic bases.

Examples of particularly suitable tertiary amines are triethylamine, tributylamine or triisopropylamine, and also pyridine or 1,8-diazabicyclo[5.4.0]undec-5-ene (DBU).

However, very particularly preferred tertiary amines are the so-called Hünig bases, which are compounds which are capable of, for example, binding hydrogen chloride, but are incapable of β-elimination.

In both reaction steps, it is possible to use a solvent, the amount as such not being critical and it being possible to use solvents such as toluene, xylene, tetrahydrofuran, dioxane, diglyme, t-butyl methyl ether, etc. Alcohols are likewise examples of suitable solvents if the alcohol radical is the same as $R^1$ and $R^2$ and Q=O. It is expedient to carry out the reactions without solvent, it being also possible for the reactants to act as solvents for one another.

The ratios of compounds of the formula II to compounds of the formula III in the first reaction step are not critical as such, and the compounds are expediently used in a stoichiometric ratio of 1:0.8 to 1.2, preferably in a ratio of 1:0.95 to 1.05, based on the equivalents.

In the second reaction step, when compounds of the formula IV are reacted with compounds of the formula V to give compounds of the formula I, the stoichiometric ratio of one equivalent of the formula IV to one equivalent of the formula V can, for example, be 1:0.8 to 1.2, preferably 1:0.95 to 1.05.

In both steps, the reaction temperatures and reaction times are not critical, and the process is as a rule carried out between 0° C. and the reflux temperature of the particular reaction mixture. It is expedient to keep the temperature between 0° C., preferably 20° C., and 40° C., preferably 35° C., when the particular reaction starts, and, towards the end of the reaction, to allow the temperature to rise between 20° C. and reflux temperature. The reaction times are as a rule between 20 minutes and 2 hours, during which process the reactants are in most cases reacted to a high degree after 20 to 40 minutes and stirring is continued for, for example, a further 20 minutes up to 1 hour. As described, the reaction as a rule proceeds in two steps. The reaction can also be controlled in such a way that it results in a one-pot process.

By way of example, the processes according to the invention follow the formulae below which have been chosen as examples:

1. First reaction step:

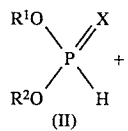

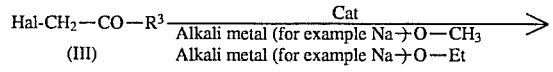

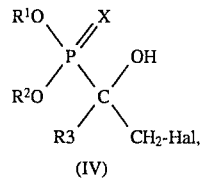

2a) Second reaction step, when, in formula I, n is 1 and $R^4$ is a monovalent radical $R^4$:

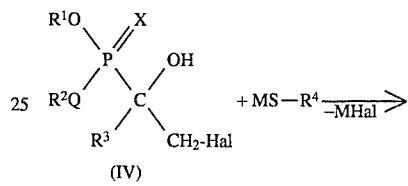

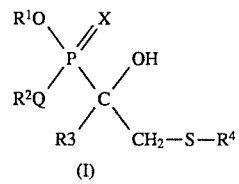

2b) Second reaction step, when, in formula I, n is 1 and $R^{4'}$ is, for example,

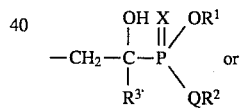

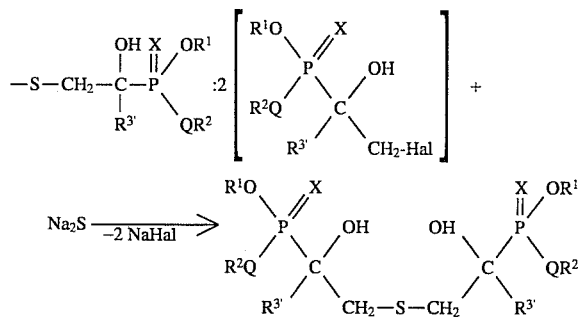

or

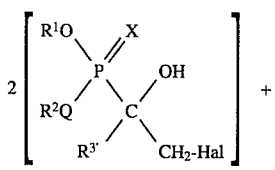

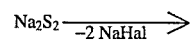

-continued

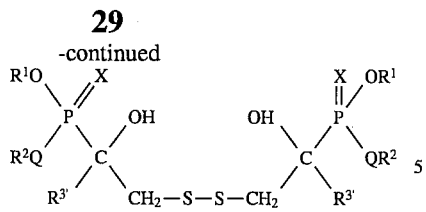

2c) Second reaction step, when, in formula I, n is 2 and, accordingly, $R^4$ is a bivalent radical:

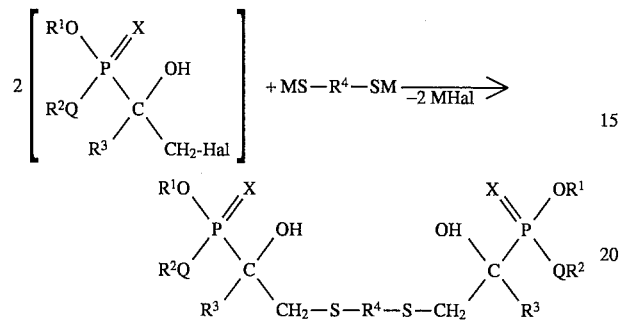

2d) Second reaction step, when, in formula I, n is 3 and, accordingly, $R^4$ is a 1,3,5-triazine radical:

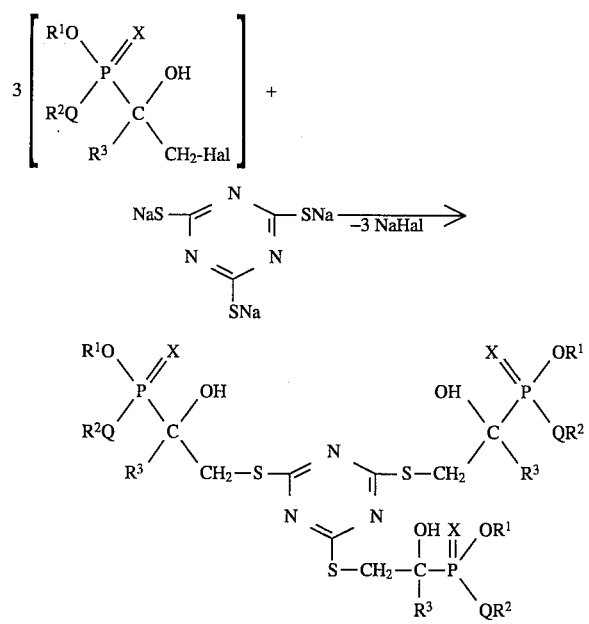

The second step can also be carried out using the corresponding alkali metal mercaptides which are readily accessible via the alkali metal alcoholates in an inert solvent.

A further example for the preparation of a series of the compounds according to the invention follows the general formulae

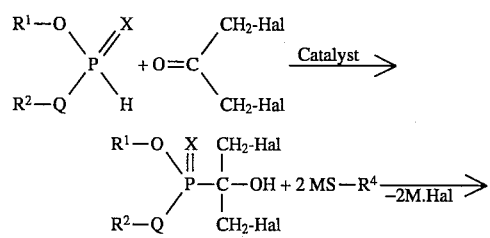

-continued

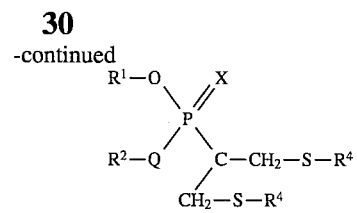

Examples of particularly preferred reactions and reaction products which can be obtained therefrom are, in the case of the first reaction step:

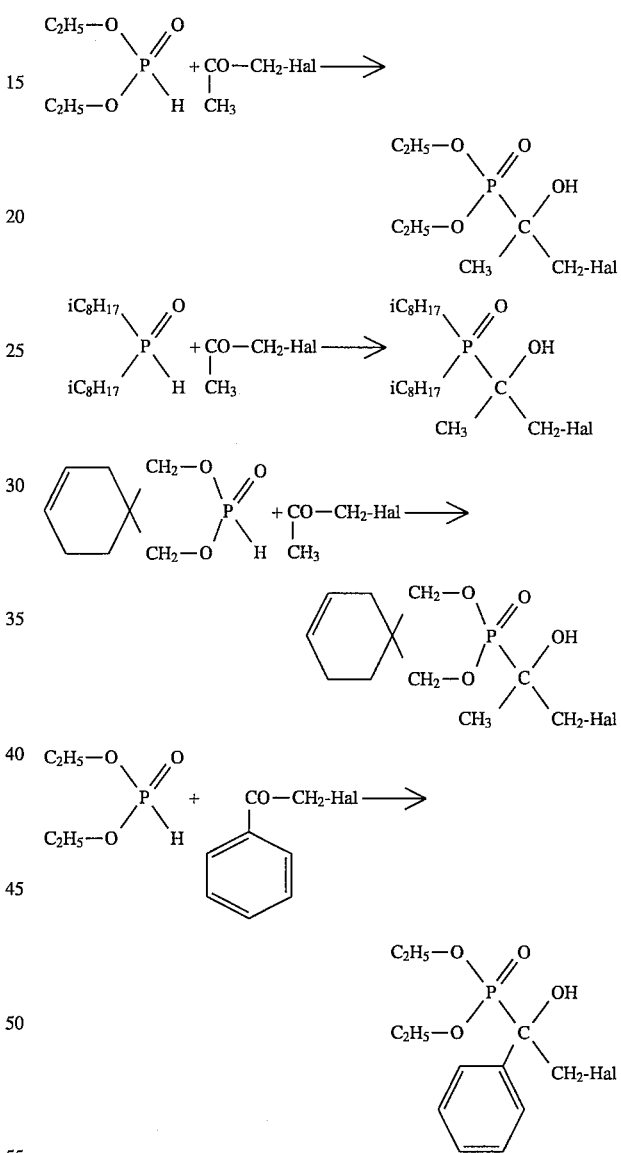

Preferred compounds can be obtained, for example, in a second reaction step by the processes described below:

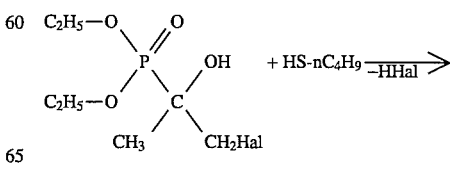

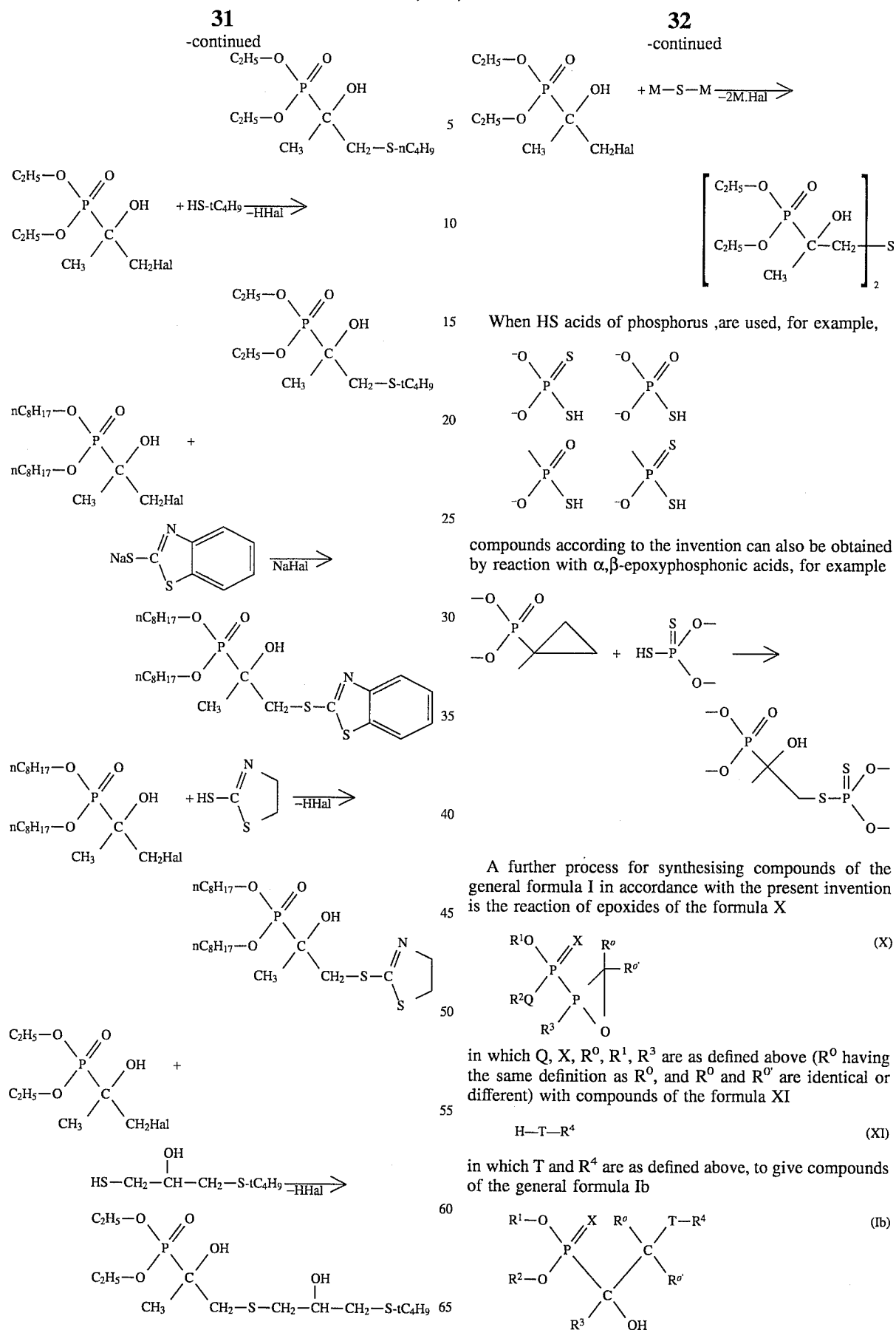

The epoxides of the formula X are known in the literature. Their preparation is described, for example, in: B. Springs and P. Haake, J. Org. Chem. 41, 1165–68 (1976), and a synopsis of further synthesis processes is given in: D. Redmore, Chem. Rev. 71,326–331 (1971).

The compounds of the general formula I in accordance with the present invention can also be obtained by a process in analogy to the description in Chemical Abstracts 67, 43873n.

In accordance with this process, for example a compound of the formula II

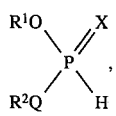   (II)

in which Q, X, R¹ and R² are as defined above is reacted with a compound of the formula VI

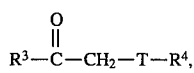   (VI)

in which T, R³ and R⁴ are as defined above, to give compounds of the general formula Ia

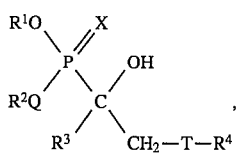   (Ia)

in which T, Q, R¹, R², R³, R⁴ and X are as defined above, in the presence of a basic catalyst.

Compounds of the formula Ia correspond to compounds of the formula I, as described above, in which Z is —H.

If n is a number 2 or 3, a corresponding compound of the formula Ia can be prepared, for example, in accordance with the following equation:

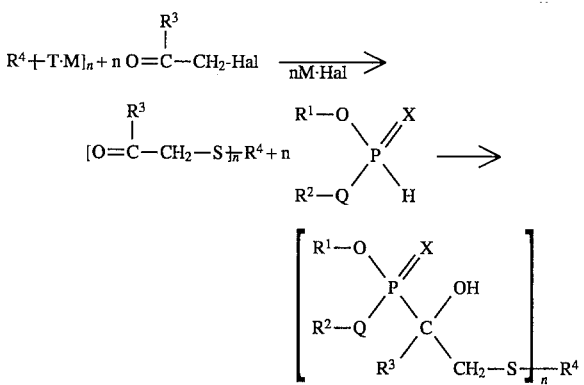

Examples of particularly preferred reactions, as described above, are:

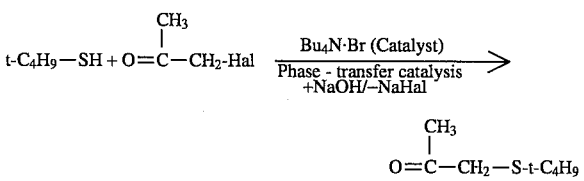

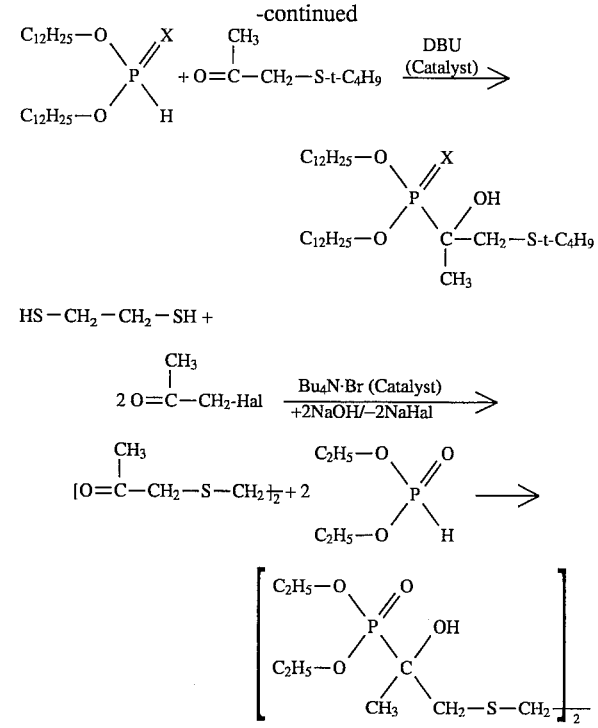

The compounds of the formula VI can be obtained, for example, by reacting a compound of the formula

R⁴—SM in which R⁴ and M are as defined above with a compound of the formula III

   (III)

in which R³ and Hal are as defined above, for example in the presence of a catalyst, expediently a basic catalyst and, in particular, a phase-transfer catalyst.

If, in compounds of the formula I, Z has a meaning other than —H, compounds of this type can be obtained, for example, by a reaction

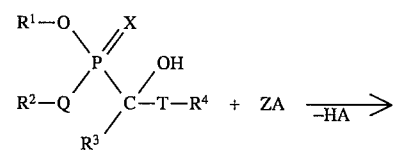

in which R¹, R², R³, R⁴, Q, X, T and Z are as defined above and A is, for example, the halogen of an acid chloride or the protone of an acid or an acyloxy group of an anhydride.

Another process variant follows, for example, the general formula

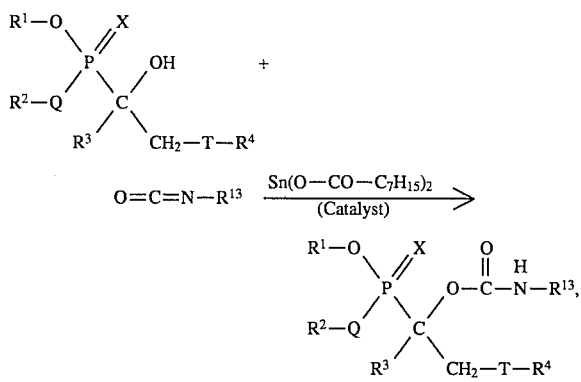

in which $R^1$, $R^2$, $R^3$, $R^4$, $R^{13}$, Q, X and T have the meanings which have been mentioned.

These reactions of —OH to give —O—$COR^{13}$, —$OCOOR^{13}$ or —$OCONHR^{13}$ can be effected in each process step in the preparation of compounds of the formula I.

electrode, 207 g of diethyl phosphite, 153 g of chloroacetone and 600 ml of toluene are cooled to 10° C. and treated with 8 ml of a sodium methylate solution (30% in methanol) with stirring and cooling. At a pH of 8, the reaction becomes exothermic, the reaction temperature rises to 34° C., stirring of the mixture is continued for 60 minutes, a slight cloudiness is removed by filtration, and the filtrate is evaporated on a rotary evaporator to give a residue.

Yield: 346 g$\hat{=}$100% of theory brown, viscous liquid, $n_D^{20}$: 1,4558

Content as per $^{31}$PNMR: 90%

The reaction mixture can be purified by distillation (b.p.$_{0.2}$:106°–107° C.; m.p. 42°–43° C.).

The compounds described in the table below are isolated analogously to the condition mentioned in Example 1.

| Example | Formula | Analytical data | Yield | Reaction medium |
|---|---|---|---|---|
| 2 | ($^iC_8H_{17}$—O—)$_2$P(=O)—C(OH)(CH$_3$)—CH$_2$—Cl | $n_D^{20}$: 1,4596 | 100% of theory $^{31P}$NMR 90% | Toluene |
| 3 | cyclohexenyl-C(CH$_2$—O)$_2$P(=O)—C(OH)(CH$_3$)—CH$_2$—Cl | m.p. 142°–43° C. | 91% of theory | Diethyl ether |
| 4 | (C$_2$H$_5$—O—)$_2$P(=O)—C(OH)(Ph)—CH$_2$—Cl | m.p. 76°–78° C. (lit. 80° C.) | 76% of theory (heptane/toluene) | Toluene |
| 5 | ($^nC_8H_{17}$—O—)$_2$P(=O)—C(OH)(CH$_3$)—CH$_2$—Cl | $n_D^{20}$: 1,4579 | 96% of theory | Toluene |
| 6 | (CH$_3$)$_2$C(CH$_2$—O)$_2$P(=S)—C(OH)(CH$_3$)—CH$_2$—Cl | m.p. 88°–89° C. | 68% of theory (petroleum ether/toluene) | Toluene |

The examples which follow illustrate the present invention in greater detail. Parts and percentages are based on the weight, unless otherwise stated.

EXAMPLE 1

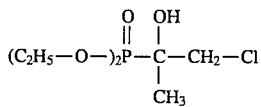

In a 1 l Sovirel flask (double-wailed reaction vessel) equipped with thermometer, stirrer, reflux condenser and pH

EXAMPLE 7

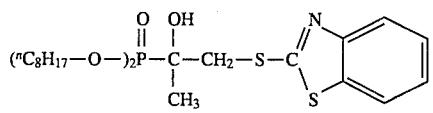

36.8 g of the compound of Example 5 are dissolved in 100 ml of tetrahydrofuran, and 18.9 g of the sodium salt of 2-mercaptobenzothiazole are added in portions, with stirring. Stirring of the mixture is then continued for 30 minutes at 20° C. and it is evaporated on a rotary evaporator to give a residue which is taken up in 150 ml of toluene. This solution is then washed with aqueous sodium bicarbonate and water, dried over sodium sulfate, and the solvent is distilled off.

Yield: 38.4 g≙78.9% of theory brown, viscous liquid, $n_D^{20}$: 1.5223

EXAMPLE 8

$$(n\text{-}C_8H_{17}\text{--}O\text{--})_2 P\text{--}\underset{\underset{CH_3}{|}}{\overset{\overset{O}{\|}\overset{OH}{|}}{C}}\text{--}CH_2\text{--}S\text{--}C\underset{\diagdown S}{\overset{\diagup N}{\diagup}\diagdown}$$

Process as described in Example 7, the sodium salt of 2-mercaptobenzothiazole is replaced by 14.1 g of the sodium salt of 2-mercaptothiazoline.

Yield: 38.5 g≙86.9% of theory brown liquid, $n_D^{20}$: 1.5015

EXAMPLE 9

$$(C_2H_5\text{--}O\text{--})_2 P\text{--}\underset{\underset{CH_3}{|}}{\overset{\overset{O}{\|}\overset{OH}{|}}{C}}\text{--}CH_2\text{--}S\text{--}^nC_4H_9$$

4.5 g of sodium are reacted in 150 ml of absolute ethanol, and this solution is then treated with 17.6 g of ⁿbutylmercaptan. 46 g of the compound of Example 1 are subsequently added dropwise to the mixture, with cooling (water bath), at 30°–35° C. in the course of 25 minutes, the mixture is heated for 30 minutes under reflux and cooled to 20° C., and the sodium chloride which has precipitated (8.1 g) are isolated. The mother liquor is evaporated to give a residue, the residue is dissolved in 150 ml of diethyl ether and washed with aqueous sodium hydrogen carbonate solution, and reconcentrated to give a residue.

The crude product (46.0 g) is subsequently purified by fractional distillation.

Yield: 28.8 g≙52% of theory, b.p.: 119°–22° C./0.3, $n_D^{20}$: 1.4696.

EXAMPLE 10

$$(C_2H_5\text{--}O\text{--})_2 P\text{--}\underset{\underset{CH_3}{|}}{\overset{\overset{O}{\|}\overset{OH}{|}}{C}}\text{--}CH_2\text{--}S\text{--}^tC_4H_9$$

Process as described in Example 9, the ⁿbutylmercaptan is replaced by ᵗbutylmercaptan.

Yield: 35.9 g≙63.1% of theory, b.p.: 108°–10° C./0.25, $n_D^{20}$: 1.4691.

EXAMPLE 11

$$\underset{CH_3}{\overset{CH_3}{\diagdown}}C\underset{CH_2\text{--}O}{\overset{CH_2\text{--}O}{\diagup}}\diagdown P\underset{\diagup}{\overset{\overset{S}{\|}}{\diagdown}}\text{--}\underset{\underset{CH_3}{|}}{\overset{\overset{OH}{|}}{C}}\text{--}CH_2\text{--}S\text{--}\underset{\underset{CH_3}{|}}{\overset{\overset{CH_3}{|}}{C}}\text{--}CH_3$$

Process as described in Example 10, the compound in accordance with Example 1 is replaced by the compound in accordance with Example 6.

EXAMPLE 12

$$(C_2H_5\text{--}O\text{--})_2 P\text{--}\underset{\underset{CH_3}{|}}{\overset{\overset{O}{\|}\overset{OH}{|}}{C}}\text{--}CH_2\text{--}S\text{--}CH_2\text{--}\overset{\overset{OH}{|}}{CH}\text{--}CH_2\text{--}S\text{-}^tC_4H_9$$

Process as described in Example 9, the ⁿbutylmercaptan is replaced by 35.2 g of ᵗC₄H₉—S—CH₂—CH(OH)—CH₂—SH.

Yield: 63.2 g≙86.5% of theory, colourless liquid. $n_D^{20}$: 1.4944.

EXAMPLE 13

$$((C_2H_5\text{--}O\text{--})_2 P\text{--}\underset{\underset{OH}{|}}{\overset{\overset{O}{\|}\overset{CH_3}{|}}{C}}\text{--}CH_2\text{--})_2 S$$

46 g of the compound of Example 1 are dissolved in 100 ml of ethanol, and 11.7 g of dehydrated sodium sulfide is introduced into this solution in portions and with stirring and cooling.

When the addition is complete, stirring of the reaction mixture is continued for 30 minutes, and the solvent is distilled off in vacuo. The residue is suspended in 200 ml of diethyl ether, extracted with 60 ml each of water and sodium bicarbonate solution, and the organic phase is dried and m-evaporated to give a residue.

Yield: 24.1 g≙57% of theory of yellow wax.

Some of this substance was recrystallised from petroleum ether (100°–140° C.).

The melting point is then 109°–111 ° C.

EXAMPLE 14

$$\left[ (^nC_8H_{17}\text{--}O\text{--})_2 P\text{--}\underset{\underset{CH_3}{|}}{\overset{\overset{O}{\|}\overset{OH}{|}}{C}}\text{--}CH_2\text{--} \right]_2 \text{--}S\text{--}\underset{S}{\overset{N\text{------}N}{\diagdown \diagup}}\text{--}S\text{--}$$

The preparation is carried out analogously to Example 13, 2 moles of the compound being reacted with 1 mole of the compound $$Na\text{--}S\text{--}\underset{S}{\overset{N\text{------}N}{\diagdown \diagup}}\text{--}S\text{--}Na$$

in accordance with Example 5. A brown, viscous liquid results, $n_D^{20}$: 1.4650.

EXAMPLE 15

$$(C_2H_5O)_2P\text{--}\underset{\underset{H_3C}{\diagup}\underset{OH}{\diagdown}}{\overset{\overset{O}{\|}}{C}}\text{--}CH_2\text{--}S\text{-}^tC_4H_9$$

Synthesis of diethyl 2-t-butylthio-1-hydroxy-1-methyl-ethanephosphonate.

8.99 g (65 mmol) of diethyl phosphite are initially introduced into 20 ml of anhydrous ethanol, and 0.90 g (5 mmol) of a 30% solution of sodium methylate in methanol is added. 8.77 g (60 mmol) of t-(butylthio)acetone are subsequently added dropwise. During this process, the internal temperature of the reaction flask rises from 24° C. to 45° C. This temperature is maintained for another 40 minutes, and the mixture is subsequently cooled, diluted with 80 ml of toluene, washed twice using 20 ml of water and dried over sodium sulfate, and the solvent is removed in vacuo.

16.2 g (95% of theory) of a pale yellow liquid remain, $n_D^{20}$: 1.4685; $^{21}$P NMR: δ=25.56 ppm (~90%)

EXAMPLE 16

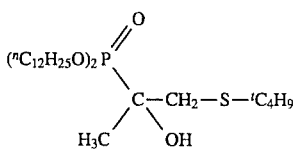

Synthesis of didodecyl 2-(t-butylthio)-1-hydroxy-1-methylethanephosphonate.

23.0 g (55 mmol) of didodecyl phosphite are initially introduced into a mixture of 20 ml of tert-butyl methyl ether and 5 ml of dimethyl sulfoxide. 1.0 g of 1,8-diazabicyclo [5.4.0]undec-5-ene (DBU) are added, and 8.04 g (55 mmol) of (t-butylthio)acetone are then added dropwise at 30° C. The reaction mixture is heated for 5 hours at 60° C., cooled, diluted with 150 ml of toluene and washed with 100 ml of water. The organic phase is dried over sodium sulfate, and the solvent and remainders of the educts are distilled off in vacuo (finally at 0.5 mbar and 55° C. bath temperature).

25.4 g (82% of theory) of a colourless, viscous liquid remain, $n_D^{20}$: =1.4609.

EXAMPLE 17

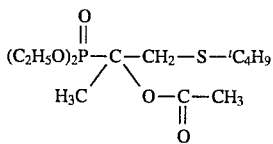

Synthesis of diethyl 1-acetoxy-2-t-butylthio-1-methylethanephosphonate 25.2 g (88.6 mmol) of diethyl 2-t-butylthio-1-hydroxy-1-methylethanephosphonate in 130 ml of acetic anhydride are treated with 1 ml of concentrated sulfuric acid, during which process the temperature of the solution rises from 20 to about 30° C. The mixture is subsequently stirred for 8 hours at 20° C., treated with 100 ml of dichloromethane and poured onto 300 ml of ice/water. The organic phase which is separated off is washed in succession with dilute hydrochloric acid, sodium hydrogen carbonate solution and water and dried over sodium sulfate, and the solvent is distilled off in vacuo.

17.4 g (60% of theory) of a pale yellow liquid with $n_D^{20}$: 1.4711 remain.

$^1$H NMR (200 MHz, CDCl$_3$): 1.76 ppm (d, CH$_3$, $J_{H,P}$= 14.9 Hz); 2.08 ppm (S, acetyl)

EXAMPLE 18

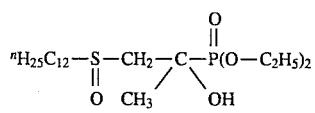

Synthesis of diethyl 2-dodecylsulfoxy-1-hydroxy-1-methylethanephosphonate 11.3 g (81.9 mmol) of diethyl phosphite and 2 ml of 1,8-diazabicyclo[5.4.0]undecene (DBU) are initially introduced into 200 ml of anhydrous tetrahydrofuran, a solution of 15.0 g (81.9 mmol) of dodecylsulfoxyacetone in 50 ml of tetrahydrofuran is added dropwise, and the mixture is subsequently refluxed for 8 hours. When the solution has cooled, it is washed twice using saturated sodium chloride solution and dried over sodium sulfate, and the solvent is distilled off, finally at 0.5 mbar and 60° C. bath temperature.

19.7 g (87% of theory) of a yellow liquid ($n_{20}^D$: 1.4741) which crystallises slowly, remain. (m.p.: 52°–53° C.).

EXAMPLE 19

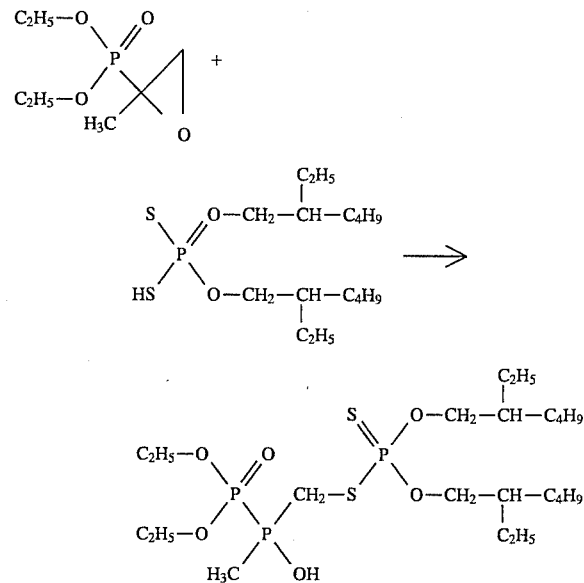

21.2 g (109 mmol) of diethyl 1,2-epoxy-1-methylethanephosphonate are initially introduced into 50 ml of toluene, under a nitrogen atmosphere. 38.7 g (109 mmol) of O,O'-bis-(2-ethylhexyl) dithiophosphate are then added dropwise at 20°–25° C. (reaction slightly exothermic). The mixture is stirred for 5 hours at 20°–25° C. and then heated for 1 hour to 40° C. to complete the reaction, and the volatile constituents are subsequently removed in vacuo. 59.9 g (100% of theory) of a colourless liquid with $n_D^{20}$: =1.4850 20 remain.

$^1$H NMR (200 MHz, CDCl$_3$): δ=3.25 ppm (ddd, 1H, C—CH$_2$—S—P,J =18.9, 13.6, 4.9 Hz); 3.54 ppm (td, 1H, C-CH$_2$—S—P, J=14.9, 7.8 Hz); 4.00 ppm (cm, 4H, CH$_2$—O—P); 4.20 ppm (cm, 4H, CH$_2$—O—P).

EXAMPLE 20

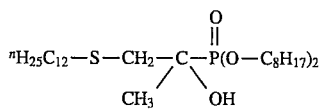

Synthesis of dioctyl 2-dodecylthio-1-hydroxy-1-methylethanephosphonate 25.6 g (83.6 mmol) of dioctyl phosphite are initially introduced into 100 ml of tert-butyl methyl ether, 0.4 g of sodium tert-butanolate are added, and 20.0 g (77.4 mmol) of dodecylthioacetone are subsequently introduced.

The solution is subsequently refluxed for 8 hours with the exclusion of moisture. After it has cooled, it is washed twice with water and dried over sodium sulfate, and the volatile components are removed in vacuo. 26.6 g (61% of theory) of a colourless viscous liquid with $n_D^{20}$ =1.4682 remain.

Further purification is possible using column chromatography with methanol/dichloromethane 1:19 on silica gel. The product which has been purified in this manner has $n_D^{20}$=1.4676.

$^1$H NMR (200 MHz, CDCl$_3$): δ=1.48 ppm (d, CH$_3$, $J_{H,P}$=15 Hz); 2.78 ppm (dd, 1H, S—CH$_2$—C(CH$_3$)(OH)—, $J_{H,H}$=14 Hz, $J_{H,P}$=7.5 Hz); 3.11 ppm (dd, 1H, S—CH$_2$—C(CH$_3$)(OH)—, $J_{H,P}$=8.5 Hz); 4.10 ppm (q, —O—CH$_2$—, J=7 Hz), (≧95%).

EXAMPLE 21

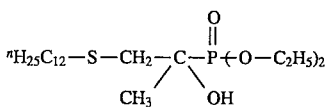

Diethyl 2-dodecylthio-1-hydroxy-1-methylethanephosphonate is likewise prepared by the above-described process, but the dioctyl phosphite is replaced by 10.6 g (76.8 mmol) of diethyl phosphite. 23.4 g (77% of theory) of crude product are obtained.

A pure product with $n_D^{20}$: =1.4680 can be obtained by column chromatography.

$^1$H NMR (200 MHz, CDCl$_3$): δ=1.48 ppm (d, CH$_3$, $J_{H,P}$=15 Hz); 2.78 ppm (dd, 1H, S—CH$_2$—C(CH$_3$)(OH)—, $J_{H,H}$=14 Hz, $J_{HP}$ =7.5 Hz); 3.11 ppm (dd, 1H, S—CH$_2$—C(CH$_3$)(OH)—, $J_{H,P}$=8.5 Hz); 4.19 ppm (q, P—O—CH$_2$—, J=7.5 Hz), (≧95%).

EXAMPLE 22

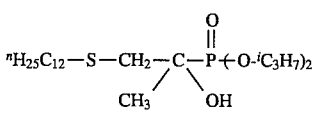

Synthesis of diisopropyl 2-dodecylthio-1-hydroxy-1-methylethanephosphonate 12.0 g (72.2 mmol) of diisopropyl phosphite and 18.6 g (72.1 mmol) of dodecylthioacetone are stirred with 5.3 g (72 mmol) of diethylamine for 72 hours and the volatile components are subsequently removed at 50° C. bath and 0.5 mbar. 30.5 g (99% of theory) of a yellow liquid with $n_D^{20}$: =1.4636 remain.

$^1$H NMR (200 MHz, CDCl$_3$): δ=1.48 ppm (d, CH$_3$, $J_{H,P}$=15 Hz); 2.75 ppm (dd, S—CH$_2$—C(CH$_3$)(OH)—, $J_{H,H}$=13.8 Hz, $J_{H,P}$= 7.5 Hz); 3.08 ppm (dd, S—CH$_2$—C(CH$_3$)(OH)—, $J_{H,P}$=8.5 Hz); 4.76 ppm (cm, —O—CH(CH$_3$)$_2$).

EXAMPLE 23

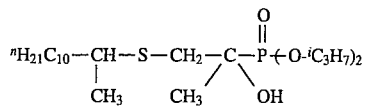

Diisopropyl 2-(1-methylundecylthio)-1-hydroxy-1-methylethanephosphonate is prepared by the process described above, dodecylthioacetone is replaced by (1-methylundecylthio)acetone. Yield 27.1 g (90% of theory) of a yellow liquid, $n_D^{20}$: =1.4593.

EXAMPLES 24–27

The ASTM Standard Method D-2783-81 is employed for testing the suitability as an anti-wear additive, using the Shell four-ball apparatus (VKA). The base oil used is Catenex® P 941, manufactured by Shell, to which 1% by weight of the compound according to the invention from the particular example mentioned is added.

The following data are determined:

a) the weld load WL as the load (in kg) at which the 4 balls weld together within 10 seconds, and b) the mean wear scar diameter at a load of 40 kg for 1 hour (in mm).

The corrosiveness towards copper is also determined, using the ASTM Standard Method D 130. For this purpose, a polished copper strip is immersed into an oil sample and remains therein for three hours at 120° C. After this test period, the copper strip is removed from the oil, cleaned and compared with the standard values. The table shows the results of 1% solutions of the particular compound according to the invention in a base oil (Catenex® P 941, manufactured by Shell), containing 0.03% of a commercially available copper passivators of the 1-(di-2-ethylhexyl)aminomethyltolutriazole type.

The copper strips are assessed in 4 steps, the "ASTM Copper Strip Corrosion Standards" being applied:
1—no tarnish
2—moderate tarnish
3—dark tarnish
4—corrosion B represents a subdivision within the key groups 1 to 4 and designates the formation of shadows on the samples. In the qualitative assessment A to E, the score A proceeds B, B proceeds C, etc.

TABLE

| Example | Compound of example | Anti-wear protection VKA | | Corrosiveness D 130 |
|---|---|---|---|---|
| | | WL kg | WSD mm | |
| 24 | 9 | 1600 | 0.34 | 1B |
| 25 | 10 | 1600 | 0.33 | 1B |
| 26 | 12 | 2000 | 0.36 | 1B |
| 27 | 7 | 2000 | 0.34 | 1B |

EXAMPLE 28

The product in accordance with Example 16 is tested for the rust-inhibiting properties in turbine oils in the presence of water, using the ASTM Standard Method D 665 B.

The set-up of the testing procedure is such that 300 ml of the test oil, containing the additives according to the invention, and 30 ml of synthetic sea water are stirred in a vessel at 60° C. for 24 hours. A cylindrical steel sample is immersed in the oil to be tested. The testing procedure is intended to determine the ability of a steam-turbine oil to prevent the rusting of iron components, in the case that water contaminates the oil.

The degree of corrosion of the steel cylinder samples is measured. 0 denotes no rust, 3 denotes a rusted sample. The scores in between accordingly denote the intermediate steps as concerns the degree of rusting.

The concentration of the compound in accordance with Example 16 is 0.25% in a base oil. After the test, the sample shows no rust and scores 0.

A sample which is tested in the base oil without compounds according to the invention is rusted and scores 3.

What is claimed is:

1. A compound of the formula I

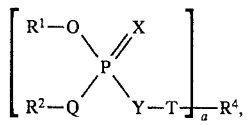

in which n is 1, 2 or 3 and in which X is oxygen or sulfur, T has the meaning of —S—, —S—S—, —S—S—S—, —S— S—S—S—, —S—S—S—S—S—,

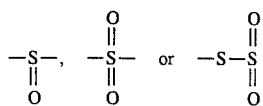

and Y has the meaning of

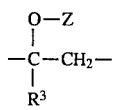

in which Z has the meaning of —H, —$COR^{13}$, —$COOR^{13}$ or —$CONHR^{43}$, and Q has the meaning of oxygen or —$NR^0$, and $R^1$, $R^2$, $R^0$ and $R^{13}$ are identical or different and are an alkyl group having 1 to 18 C atoms, an alkenyl group having 2 to 18 C atoms, a phenyl or naphthyl group, a phenyl or naphthyl group each of which is substituted by at least one $C_1$-$C_4$alkyl group, or are a phenylalkyl group having 7 to 9 C atoms, a cycloalkyl group having 5 to 12 ring C atoms or a cycloalkyl group having 5 to 12 ring C atoms which is substituted by at least one alkyl group having 1 to 4 C atoms, or $R^0$ is —H, or $R^1$ and $R^2$ together are a straight-chain alkylene group having 2 to 5 C atoms, a straight-chain alkylene group having 2 to 5 C atoms which is substituted by at least one alkyl group having 1 to 8 C atoms or by at least one group —$CH_2$—O—$C_1$-$C_{12}$alkyl or —$CH_2$—S—$C_1$-$C_{12}$alkyl, or $R^1$ and $R^2$ together are a group of the formula

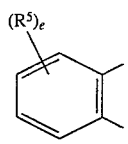

in which $R^5$ is an alkyl group having 1 to 4 C atoms and e is a number 0, 1 or 2, or $R^1$ and $R^2$ together are a group of the formula

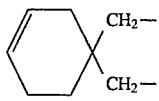

$R^3$ has the meaning of —H, alkyl having 1 to 4 C atoms, phenyl, —$CH_2$—S—$R^{4'}$, in which $R^{4'}$ is as defined below, or is phenyl or phenyl substituted by at least one alkyl group having 1 to 4 C atoms, and, if n is 1, $R^4$ has the meaning of $R^{4'}$ in which $R^{4'}$ is —H, an alkyl group having 12 to 18 C atoms, an alkenyl group having 2 to 18 C atoms pinan-10-yl, an alkyl group having 1 to 18 C atoms which is substituted by at least one OH group, an alkyl group having 2 to 18 C atoms which is interrupted by at least one —S— or —O—, an alkyl group having 3 to 18 C atoms which is substituted by at least one OH group and interrupted by at least one —S— or —O—, a group of the formula —$R^6$—$COOR^7$ in which $R^6$ is an alkylene group having 1 to 6 C atoms and $R^7$ is an alkyl group having 1 to 12 C atoms; a cycloalkyl group having 5 to 12 ring C atoms, a cycloalkyl group having 5 to 12 ring C atoms which is substituted by at least one alkyl group having 1 to 4 C atoms, or is a cycloalkyl group having 5 to 12 ring C atoms which is interrupted by at least one —O— or —S—, or is a cycloalkyl group having 5 to 12 ring C atoms which is substituted by at least one alkyl group having 1 to 4 C atoms and interrupted by at least one —O— or —S—, or $R^{4'}$ is a group of the formula

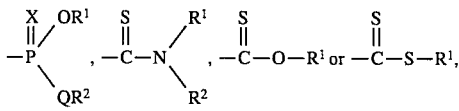

in which X is oxygen or sulfur and Q, $R^4$ and $R^2$ are as defined above, or $R^4$ is a heterocycle having 5 to 6 ring members with 1 to 4 members selected from the group consisting of —NH—, —N=,

and —N($C_1$-$C_4$alkyl)—, or a heterocycle having 5 to 6 ring members with one or two members from the group consisting of —NH—, —N=,

or —N($C_1$-$C_4$alkyl)— and one further hetero atom selected from the group consisting of O and S, or the abovementioned heterocycles which are fused to a benzene radical, or the abovementioned heterocycles which are substituted on one or two of the C atoms by =S and/or $C_1$-$C_4$alkyl, or $R^{4'}$ has the meaning of

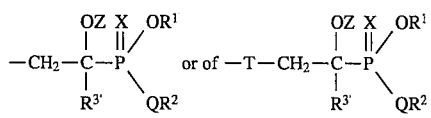

in which T and Z are as defined above, X is oxygen or sulfur, $R^{3'}$ is —H, alkyl having 1 to 4 C atoms, phenyl or phenyl which is substituted by at least one alkyl group having 1 to 4 C atoms, and Q, $R^1$ and $R^2$ are as defined above, or $R^4$ has the meaning of

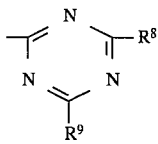

in which $R^8$ and $R^9$, independently of one another, are $C_1$–$C_{18}$alkyl, phenyl, phenyl which is mono-, di- or tri-$C_1$–$C_4$alkyl-substituted, or are a group —$OR^{10}$, —$SR^{10}$ or

in which $R^{10}$ is $C_1$–$C_{18}$alkyl, $C_5$–$C_{12}$cycloalkyl, $C_5$–$C_{12}$cycloalkyl which is mono-, di- or tri-$C_1$–$C_4$alkyl-substituted, or is $C_3$–$C_6$alkenyl, phenyl, phenyl which is mono-, di- or tri-$C_1$–$C_9$alkyl-substituted, or is $C_7$–$C_9$phenylalkyl or $C_7$–$C_9$phenylalkyl which is mono-, di- or tri-$C_1$–$C_4$alkyl-substituted on the phenyl, and $R^{11}$ and $R^{12}$ which are identical or different are —H, $C_1$–$C_{18}$alkyl, $C_5$–$C_{12}$cycloalkyl, $C_5$–$C_{12}$cycloalkyl which is mono-, di- or tri-$C_1$–$C_4$alkyl-substituted, or are $C_3$–$C_6$alkenyl, $C_7$–$C_9$phenylalkyl, $C_7$–$C_9$phenylalkyl which is mono-, di- or tri-$C_1$–$C_4$alkyl-substituted on the phenyl, or are $C_2$–$C_4$alkyl which is substituted by —OH, by $C_1$–$C_8$alkoxy or by di($C_1$–$C_4$alkyl)amino, or $R^{11}$ and $R^{12}$ together with the nitrogen atom linking them are a 5- to 7-membered heterocycle, or, if n is 2, $R^4$ is straight-chain alkylene having 1 to 12 C atoms or alkenylene having 2 to 10 C atoms or straight-chain alkylene having 1 to 10 C atoms which is substituted by at least one alkyl group having 1 to 4 C atoms, or straight-chain alkylene having 2 to 10 C atoms which is interrupted by at least one —S— or —O—, or straight-chain alkylene having 2 to 10 C atoms which is substituted by at least one alkyl group having 1 to 4 C atoms and interrupted by at least one —S— or —O—, or $R^4$ has the meaning of a bivalent heterocycle having 5 to 6 ring members with 1 to 4 nitrogen atoms, or of a bivalent heterocycle having 5 to 6 ring members with one or two nitrogen atoms and one further hetero atom selected from the group consisting of O or S, or of the abovementioned bivalent heterocycles which are substituted by =S and/or $C_1$–$C_4$alkyl on one or two of the C atoms, or, $R^4$ has the meaning of

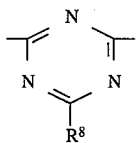

in which $R^8$ is as defined above, or, if n is 3, $R^4$ is a group of the formula

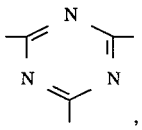

with the proviso that the compound of the formulae $C_2H_5$—S—$CH_2CH(OH)$—PO(—$OC_2H_5$)$_2$, Ph—C(CH$_2SCH_3$)(OH)—PO(—$OC_2H_5$)$_2$ and $C_2H_5$—S—$CH_2CH(OC(O)CH_3)$—PO(—$OC_2H_5$)$_2$ are excepted.

2. A compound of the general formula I according to claim 1, in which n is 1, 2 or 3, and in which $R^1$ and $R^2$ are identical or different and are an alkyl group having 1 to 18 C atoms, an alkenyl group having 2 to 18 C atoms, a phenyl group, a phenyl group which is substituted by one or two $C_1$–$C_9$alkyl groups, or are a phenylalkyl group having 7 to 9 C atoms, a cycloalkyl group having 5 to 12 ring C atoms or a cycloalkyl group having 5 to 12 ring C atoms which is substituted by an alkyl group having 1 to 4 C atoms, or in which $R^1$ and $R^2$ together are a straight-chain alkylene group having 2 to 5 C atoms, a straight-chain alkylene group having 2 to 5 C atoms which is substituted by one or two alkyl groups having 1 to 4 C atoms or by a group —$CH_2$—O—$C_1$–$C_9$alkyl or —$CH_2$—S—$C_1$–$C_9$alkyl, or $R^1$ and $R^2$ together are a group of the formula

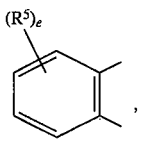

in which $R^5$ is an alkyl group having 1 to 4 C atoms and e is a number 0, 1 or 2, or $R^1$ and $R^2$ together are a group of the formula

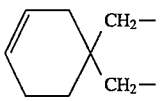

$R^3$ has the meaning of —H, alkyl having 1 to 4 C atoms, —$CH_2$—S—$R^{4'}$ in which $R^{4'}$ is as defined below, phenyl or phenyl which is substituted by an alkyl group having 1 to 9 C atoms, and, if n is 1, $R^4$ has the meaning of $R^{4'}$ in which $R^{4'}$ is —H, an alkyl group having 12 to 18 C atoms, an alkenyl group having 2 to 18 C atoms, an alkyl group having 1 to 18 C atoms which is substituted by 1 to 5 OH groups, an alkyl group having 2 to 18 C atoms which is interrupted by 1 to 5 —S— or —O—, an alkyl group having 3 to 18 C atoms which is substituted by 1 to 5 OH groups and interrupted by 1 to 5 —S— or —O—, a cycloalkyl group having 5 to 12 ring C atoms, a cycloalkyl group having 5 to 12 ring C atoms which is substituted by an alkyl group having 1 to 4 C atoms, or R$^{4'}$ is a group of the formula

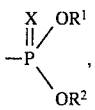

in which X is oxygen or sulfur and R$^1$ and R$^2$ are as defined above, or

R$^{4'}$ has the meaning of a heterocycle having 5 to 6 ring members with 1 to 3 members from the group consisting of —NH—, —N=,

and —N(CH$_3$)— or of a heterocycle having 5 to 6 ring members with one member from the group consisting of —NH—, —N=,

and —N(CH$_3$)— and one further hetero atom from the group consisting of O and S, or of the abovementioned heterocycles which are fused to a benzo radical, or of the abovementioned heterocycles which are substituted on one or two of the C atoms by =S and/or C$_1$–C$_4$alkyl, or, if n is 2, R$^4$ is straight-chain alkylene having 1 to 10 C atoms or straight-chain alkylene having 1 to 10 C atoms which is substituted by one or two alkyl groups having 1 to 4 C atoms, or straight-chain alkylene having 2 to 10 C atoms which is interrupted by 1 to 5 —S— or —O—, or alkylene having 2 to 10 C atoms which is substituted by one or two alkyl groups having 1 to 4 C atoms and interrupted by 1 to 5 —S— or —O—, or R$^4$ has the meaning of a bivalent heterocycle having 5 to 6 ring members with 1 to 3 nitrogen atoms, or of a bivalent heterocycle having 5 to 6 ring members with one or two nitrogen atoms and one further hetero atom from the group consisting of O and S, or of the abovementioned bivalent heterocycles which are fused to a benzo radical, or of the abovementioned bivalent heterocycles which are substituted on one or two of the C atoms by =S and/or C$_1$–C$_4$alkyl, or, if n is 3, R$^4$ is a group of the formula

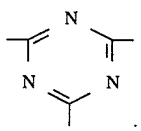

3. A compound according to claim 1, of the formula I in which R$^1$ and R$^2$ are identical or different and are a straight-chain or branched-chain alkyl group having 2 to 12 C atoms, phenyl, phenyl which is substituted by one C$_1$–C$_9$alkyl group, benzyl, or a cycloalkyl group having 5 to 10 ring C atoms, or in which R$^1$ and R$^2$ together are a straight-chain alkylene group having 2 to 4 C atoms or a straight-chain alkylene group having 2 to 4 C atoms which is substituted by one or two alkyl groups each of which has 1 to 4 C atoms, or which is substituted by a group of the formula —CH$_2$—S—C$_4$H$_9$, or are a group of the formula

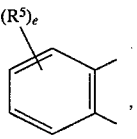

in which e is 0 or 1 and, if e is 1, R$^5$ is tert-butyl.

4. A compound according to claim 1, of the formula I in which R$^1$ and R$^2$ are identical or different and are an alkyl group having 2 to 12 C atoms, phenyl or cyclohexyl, or R$^1$ and R$^2$ together are a straight-chain C$_2$- or C$_3$-alkylene group, or are a dimethylene or trimethylene group which is substituted by a C$_1$–C$_4$alkyl group, or are a di-C$_1$–C$_4$alkyl-substituted dimethylene or trimethylene group or a —CH$_2$—S—t—C$_4$H$_9$-substituted dimethylene or trimethylene group, or a group of the formula

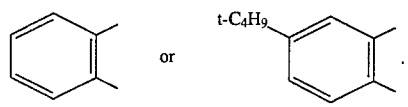

5. A compound according to claim 1, of the formula I in which R$^1$ and R$^2$ are identical or different and are C$_2$–C$_8$alkyl, or R$^1$ and R$^2$ together are dimethylene, 1-methyldimethylene, 1-ethyldimethylene, 2,2-dimethyltrimethylene or 2-ethyl-2-n-butyltrimethylene.

6. A compound according to claim 1, of the formula I in which R$^1$ and R$^2$ are identical.

7. A compound according to claim 1, of the formula I in which R$^3$ is methyl, phenyl or —CH$_2$—S—R$^{4''}$ in which R$^{4''}$ is an alkyl group having 2 to 12 C atoms or

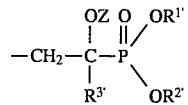

in which Z is as defined in claim 1 and R$^{3'}$ is —H, alkyl having 1 to 4 C atoms or phenyl, and R$^{1'}$ and R$^{2'}$ are identical and an alkyl group having 1 to 8 C atoms, phenyl or cyclohexyl, or R$^{R'}$ and R$^{2'}$ together are a straight-chain C$_2$- or C$_3$-alkylene group or a C$_1$–C$_4$alkyl-substituted dimethylene or trimethylene group, a di-C$_1$–C$_4$alkyl-substituted dimethylene or trimethylene group or a —CH$_2$—S—t—C$_4$H$_9$— or —CH$_2$—O—iC$_8$H$_{17}$-substituted dimethylene or trimethylene group.

8. A compound according to claim 18, of the formula I in which R$^{4'}$ is an alkyl group having 12 C atoms or an alkyl group having 2 to 8 C atoms which is substituted by an OH group or an alkyl group having 2 to 12 C atoms which is interrupted by an —O— or —S—, or an alkyl group having 2 to 18 C atoms which is interrupted by an —O— or —S— and substituted by an —OH group, or a group of the formula —R$^6$—COOR$^7$ in which R$^6$ is an alkylene group having 1 to 3 C atoms and R$^7$ is an alkyl group having 4 to 8 C atoms, or is a cyclohexyl group, or R$^{4'}$ is a group of the formula

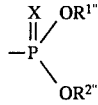

in which X is oxygen or sulfur and R$^{1''}$ and R$^{2''}$ are identical and are alkyl having 1 to 8 C atoms or R$^{4''}$ and R$^{2''}$ together are straight-chain alkylene having 2 or 3 C atoms or straight-chain alkylene having 2 or 3 C atoms which is substituted by one or two alkyl groups having 1 to 4 C atoms, or $R^{4'}$ has the meaning of a heterocycle having 5 to 6 ring members with 1 to 3 nitrogen atoms, or of a heterocycle having 5 to 6 ring members with one nitrogen atom and one further hetero atom from the group consisting of O and S, or of the abovementioned heterocycles which are fused to a benzo radical, or of the abovementioned heterocycles which are substituted on one or two of the C atoms by =S or by $C_1$–$C_4$alkyl, or $R^{4'}$ has the meaning of

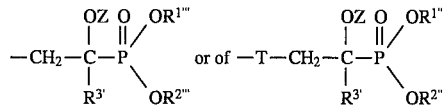

in which T and Z are as defined in claim 1, $R^{3'}$ is methyl and $R^{1'''}$ and $R^{2'''}$ are identical and are alkyl having 1 to 8 C atoms.

9. A compound according to claim 18, of the formula I in which n is 2 and in which $R^4$ is straight-chain alkylene having 2 to 4 C atoms or $R^4$ has the meaning of a divalent heterocycle having 5 to 6 ring members with one or two nitrogen atoms and one further hetero atom from the group consisting of O and S.

10. A compound according to claim 18, of the formula I in which n is 1, $R^1$ and $R^2$ are identical and are $C_1$–$C_{12}$alkyl, or $R^1$ and $R^2$ together are

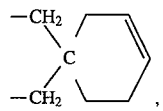

$R^3$ has the meaning of $C_1$–$C_4$alkyl or phenyl, and $R^4$ has the meaning of $R^{4'}$ in which $R^{4'}$ is a heterocycle having 5 ring members and one or two nitrogen atoms, a heterocycle having 5 ring members and one nitrogen atom and with one or two additional hetero atoms from the group consisting of S and O, one of the abovementioned heterocycles with fused benzo ring, or $C_3$–$C_{12}$alkyl which is substituted by one —OH and interrupted by 1 or 20 or S.

* * * * *